(12) United States Patent
Claps

(10) Patent No.: US 7,783,458 B2
(45) Date of Patent: Aug. 24, 2010

(54) DISCRETE PRINCIPAL COMPONENT ANALYSIS (DPCA)

(76) Inventor: Ricardo Claps, 329 N. First St., Apt. No. 311, San Jose, CA (US) 95110

( * ) Notice: Subject to any disclaimer, the term of this patent is extended or adjusted under 35 U.S.C. 154(b) by 254 days.

(21) Appl. No.: 11/767,458

(22) Filed: Jun. 22, 2007

(65) Prior Publication Data

US 2008/0319712 A1 Dec. 25, 2008

(51) Int. Cl.
*H03F 1/26* (2006.01)
(52) U.S. Cl. .................................................. 702/189
(58) Field of Classification Search .................. 702/189
See application file for complete search history.

(56) References Cited

U.S. PATENT DOCUMENTS

| 7,245,373 | B2* | 7/2007 | Soller et al. | 356/325 |
| 2002/0053545 | A1* | 5/2002 | Greef | 210/656 |
| 2007/0038041 | A1* | 2/2007 | Yang et al. | 600/310 |

OTHER PUBLICATIONS

"A Mathematical Theory of Communication", C.E. Shannon, Reprinted with corrections form *The Bell System Technical Journal.* vol. 27, pp. 379-423, 623-656, Jul., Oct. 1948 (55 pages).
"Statistics of Atomic Frequency Standards", David W. Allan, Proceedings of the IEEE, vol. 24, No. 2, Feb. 1966 (10 pages).
"Some Notes on Entropy Measures", I. Lerche, Mathematical Geology, vol. 19, No. 8, Feb. 1987 (11 pages).
"Some Notes on Entropy Measures. II. The Relative Entropy Matrix and the Positivity Constraint", Ian Lerche, Mathematical Geology, vol. 21, No. 8, May 1989 (10 pages).
PCT International Search Report and Written Opinion dated Sep. 29, 2008.

* cited by examiner

*Primary Examiner*—Aditya Bhat
(74) *Attorney, Agent, or Firm*—Haynes and Boone, LLP; Edward C. Kwok

(57) ABSTRACT

An optical system employs filtered broad band light for determining the specific components in a material sample. The system forms an r by n matrix C representing r principal components of the measurement to be analyzed at n different frequencies. Each sample contains a known quantity of the different materials in the sample being analyzed where r represents the number of different analytes or components in the sample. The system measures m different samples at n different frequencies, said m samples containing unknown quantities of the material, where "m" is a selected integer representing the number of samples. Using the measured results from the m samples the system forms an n by m matrix P, where P=C·R, and where R is an m by r matrix representing r unknown values of the r principal components which are being measured in the m material samples. The system then solves the equation P=C·R for R by inverting C in the equation $$R = (C^T \cdot C)^{-1} \cdot C^T \cdot P.$$

This gives the value of each of the r principal components in the sample.

42 Claims, 23 Drawing Sheets

| $\lambda_c$ | $\Delta_\lambda$ | $1-\kappa$ |
|---|---|---|
| 947 | 155 | 0.33 |
| 1235 | 154 | 0.39 |
| 1446 | 51 | 0.24 |
| 1619 | 99 | 0.41 |
| 1748 | 107 | 0.28 |
| 1986 | 110 | 0.75 |
| 2202 | 94 | 0.02 |
| 2352 | 124 | 0.17 |

Key to FIG. 13

| Fig. 13A | Fig. 13B |

DISCRETE PRINCIPAL COMPONENT ANALYSIS (DPCA)

FIELD OF THE INVENTION

This invention relates to structures and methods for implementing the well-known technique of Principal Component Analysis using an algorithm called Discrete Principal Component Analysis in a reduced parameter space with high computational efficiency. More particularly, this invention makes it possible to implement the technique using simple and low-cost hardware both in the sensor and the transducer (for example, using hardware such as photo-detector arrays, camera arrays and similar detectors).

RELATED PATENTS AND APPLICATIONS

This invention relates to application Ser. No. 11/185,138 filed Jul. 20, 2005 entitled "Optical Monitoring System with Molecular Filters", assigned to Neptec Optical Solutions, Inc., and the University of Kentucky Research Foundation, application Ser. No. 11/185,138 is hereby incorporated by reference herein in its entirety.

BACKGROUND

The measurement of the characteristics of complex systems is a challenge particularly if the measurements must be carried out rapidly in the real world as opposed to a laboratory environment. Usually complex systems, such as compounds containing many constituents, must be analyzed in a laboratory using sensitive and expensive equipment. As a result, with measurement systems of the type used in laboratories, it is not possible to determine in a very short time the constituents of materials or compounds outside of the laboratory. Moreover, these prior art systems, such as a typical grating-based spectrometer, utilize a large number of channels, such as 256, 512 or 1024 channels. This makes these instruments expensive and requires the use of high end computation equipment to process the data. What is needed is a fast and cost efficient system which allows one to determine the constituents of materials or compounds, for example, outside of the laboratory.

SUMMARY

In accordance with this invention, the constituents of complex systems are measured by optical means, in a fast, cost efficient manner. By "complex systems" is meant systems with multiple components to be measured, either in the chemical sense, in the geometric sense, or in any combination of both. The optical means of measurement may be spectroscopic (separating light by wavelength), interferometric (separating light by phase), intensity-based, imaging-based, or any combination of these. The speed and simplicity of measurement associated with systems operating in accordance with this invention means that this invention can be used in a broad variety of field applications or in applications where the details of the measurement procedure provide new information on a given phenomenon.

The structures and methods of this invention allow one to achieve a significant reduction in the cost of measuring the constituents of complex systems while simultaneously decreasing the time required to make these measurements.

This invention will be more fully understood in view of the following detailed description taken together with the following drawings.

DESCRIPTION OF THE DRAWINGS

FIG. 8A shows one double-step, consisting of a single "shell" calculation and a series of "cloud" point calculations. FIG. 8B shows the resulting trajectory from the initial point, $\vec{r}_0$, to the final point, $\vec{r}_P$, where P is the total number of double-steps (or "shells") considered. FIG. 8C shows the flow diagram for the software routine implemented for the method.

DETAILED DESCRIPTION

Figure 1:
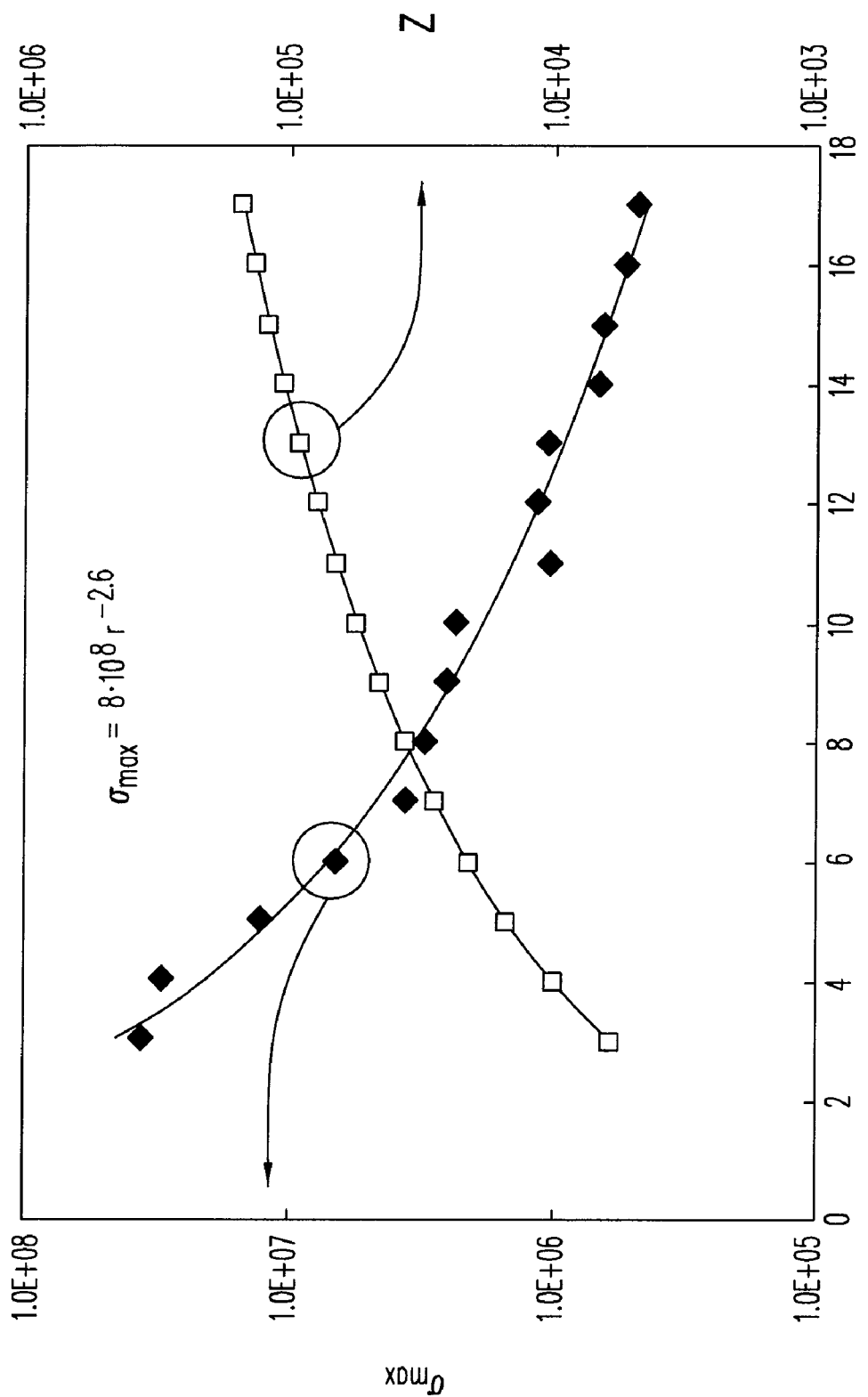
FIG. 1 shows the variance of the solution as a function of the number of principal components, r, compared to the number of calculations, Z, needed to solve the problem (namely to find the concentrations of Cholesterol, Collagen and Elastin in a given sample of blood using Molecular Factor Computation and Near Infrared absorption spectroscopy)

The following description is illustrative only. Other embodiments of this invention will be obvious in view of this disclosure.

In the most general mode, a set of n measurements performed on m different samples can be organized in the form of an n×m matrix, P. Principal Component Analysis (PCA) is a mathematical algorithm that makes use of basic linear algebra operations in order to rewrite any given n×m matrix, P, in the form:

$$P = C \cdot R \quad (1)$$

In equation (1), C is an n×r matrix, representing the calibration of the system with known values of the principal components, and R is an r×m matrix, representing the unknown composition of the said principal components in the sample being measured. For example, in one embodiment of this invention, matrix C can be associated with a general set of properties of the measurement strategy, i.e. a quality of the measurement that remains constant from one measurement to the next, and matrix R can be associated with a specific property of the sample being analyzed. For example, a sample could be a solution containing a number of constituents. In one embodiment, each constituent is a principal component. For example, if the sample is blood, the constituents (i.e. the principal components) could include red blood cells, white blood cells, glucose and cholesterol among others. The elements of matrix R are the actual properties of the sample that need to be determined by the measurement. For purely practical reasons, matrix R will be referred to as the "concentrations" matrix. In some applications of this technique, the values of this matrix may refer to the specific concentrations of the different constituents (sometimes also called "analytes") in a given sample. In other applications, the values of the numbers in the concentration matrix, R, may refer to the probability or likelihood for a given image to be a representation of a known object. The r columns of matrix C are called "loading vectors" and correspond to the "Principal Components" of the measurement configuration. Equation (1) establishes clearly that a linear relation exists between the "concentrations" in the experiment, R, and the measurement results, P. This is a fundamental hypothesis of PCA and its validity needs to be verified on each case it is applied. A verification technique will be discussed below in conjunction with FIG. 10.

Once matrix C is determined, then solving Eq. (1) for R is straightforward, as in:

$$R = (C^T \cdot C)^{-1} \cdot C^T \cdot P \quad (2)$$

In Eq. (2), it is assumed that the matrix, $\xi \equiv (C^T \cdot C)$, is non-singular (otherwise, the matrix C is ill-defined and the measurement strategy needs revision). Note that the procedure described by Eqs. (1) and (2) is quite general and involves a measurement that can be as detailed as desired, since matrices P (measurement) and R are two-dimensional arrays of data. Matrix C is formed by previous knowledge of the experimental conditions in which the measurement will be carried out. This procedure could imply, but is not limited to, using a given number of sampling measurements or calibrations, with known concentrations, $\tilde{R}$. One example of this could be in the problem of measuring glucose concentrations in blood or water solutions using Near Infrared Spectroscopy (NIR). A calibration procedure starts by measuring a control set of glucose solutions in blood or water, e.g. 70 different samples with monotonically increasing, known glucose concentrations, everything else remaining the same in the experiment. Labeling the calibration concentrations and calibration measurements as $\tilde{R}$ and $\tilde{P}$, respectively, we can find C, from Eq. (1), as $$C = \tilde{P} \cdot \tilde{R}^t (\tilde{R} \cdot \tilde{R}^t) \quad (3)$$

The total number of operations, Z, required to solve Eqs. (1) and (2), is given by:

$$Z = r^3 + r^2 \cdot n + r \cdot n \cdot m. \quad (4)$$

Equation (4) can be derived from the principles discussed in the book by Kevin R. Wadleigh and Isom L. Crawford entitled "Software Optimization for High-Performance Computing" published in May 18th, 2000, by Prentice Hall, ISBN-10: 0-13-017008-9. In equation (4), r is the number of principal components, that is, the number of constituents in the sample, and n is the number of individual measurements taken for each sample. For example, n could be the number of pixels in a photo-detector array, each pixel collecting light corresponding to a specific wavelength unique to that pixel, or a specific portion of the object being imaged. The number of measurements on the samples collected during the experiment is expressed by "m". Typically, this number will be one (1), since the analysis is performed only at one location at a given time. However, a more complex sensor architecture can be envisioned where measurements of different samples are taken simultaneously, or measurements of the same sample at different times are considered in the same analysis, in which case the number "m" may be much larger than 1. The measurement of a sample containing r principal components will be described below in conjunction with the structure of FIG. 5C.

It is seen that the complexity of the calculation routine increases dramatically as the number of principal components (also called "loading vectors"), r, grows. However, the variance of the results, $\sigma_{max}$, reduces at about the same rate, as a function of r. This results from the dependence of R on the matrix $\xi^{-1}$, shown in Eq. (2). Here, the variance of a multiple set of components will be defined as the square root of the sum of the variance squared for each of the components: $\sigma = \sqrt{\sigma_1^2 + \ldots + \sigma_k^2}$. FIG. 1 illustrates the two competing effects, where the parameter $\sigma_{max}$ is proportional to the maximum possible determinant that can be found for a specific problem with a 3-component vectorial solution. On the other hand, of the three parameters, r, n, m, in Eq. (4), typically the largest one is the dimension of the coordinate space, n. This also happens to be the parameter that is more costly, from the hardware point of view. Each of the entries in this space is a data point collected by some photo-sensitive device, either a pixel in a CCD or CMOS detector array, or a photodetector coupled to an electrical step-scanner of some sort.

Figure 2A:
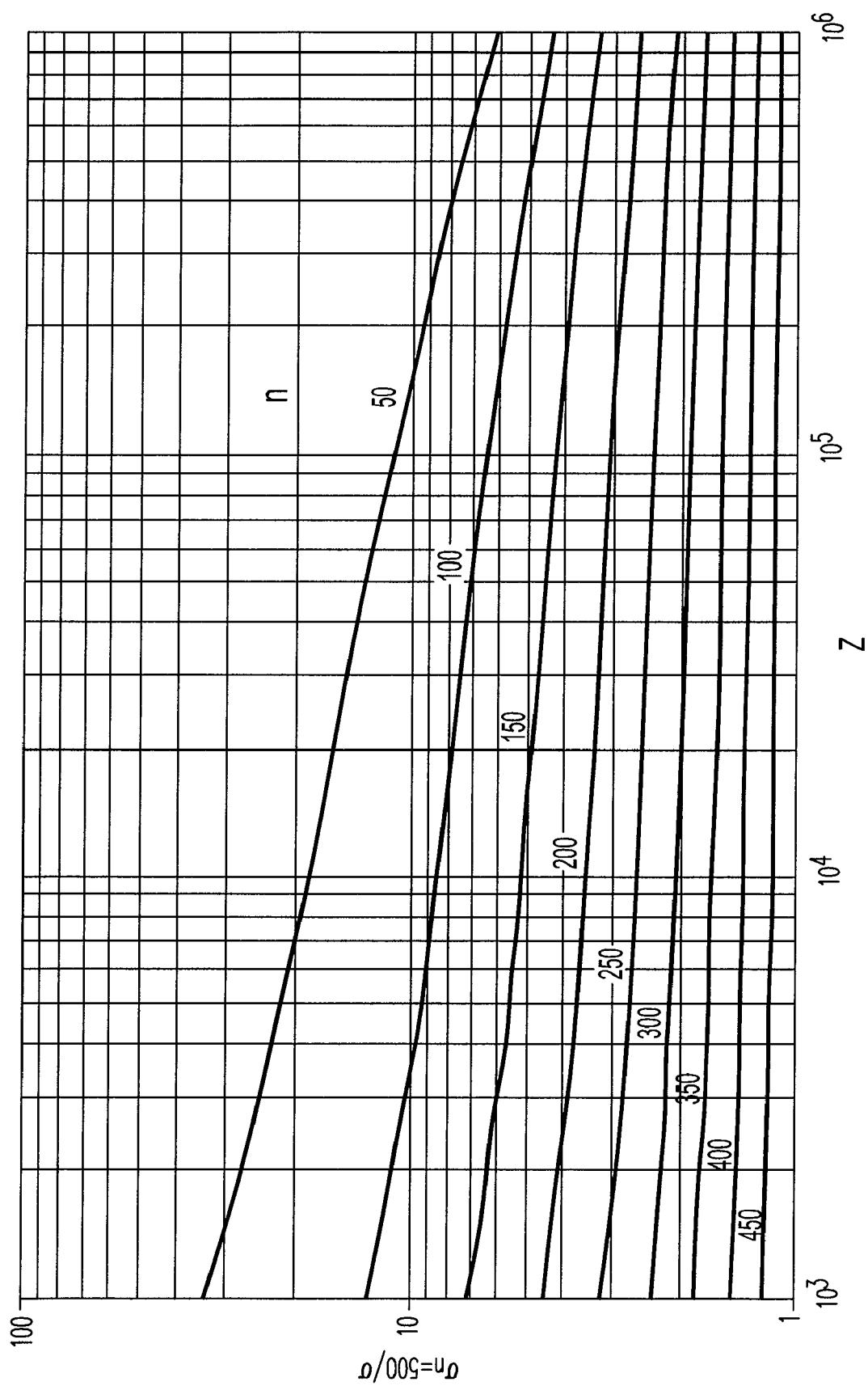
FIGS. 2A and 2B show the relative variance in the measurement of the samples discussed in FIG. 1, as a function of the number of calculations for different values of n, where n is the number of measurement channels (FIG. 2A), and the entropy variance as a function of the number of channels for the same problem (FIG. 2B)

In accordance with the present invention, PCA techniques are used with a parameter space, n, dramatically reduced by one or more orders of magnitude. Sometimes the parameter space is referred to by its "dimensionality", i.e. the number of channels n, which always corresponds to the number of individual measurements taken for one sample (provided the sample is run through the hardware which does the measurements only once). This will not only reduce the number of operations needed to perform any given calculation, but also dramatically reduce the costs and complexity of measurement strategies. FIG. 2A shows the effect of reducing the dimensionality of the coordinate space, n, for the same problem illustrated in FIG. 1, above. By taking n=500 as a point of comparison (the NIR spectra used to collect the data for FIGS. 1 and 2 have dimension 500), FIG. 2A plots the variation in relative variance as a function of the number of calculations Z. FIG. 2A shows that, for a fixed number of operations, the precision of the calculation, relative to that corresponding to n=500, is increased by almost 2 orders of magnitude as the dimensionality, n, is reduced by a similar factor. The reason for this is that with a lower dimensionality, n, it is possible to increase the number of principal components, r, without compromising the total number of calculations, Z. Since the precision of the measurement technique is proportional to r (FIG. 1), the results shown in FIG. 2A follow. Here, and for the rest of this application, the term "precision" is a function of the variance in the measurement. The larger the variance, the poorer the precision of the measurement. Another important consequence can be deduced from FIG. 2A. FIG. 1 shows that as the number of principal components, r, in the sample being considered in the measurement is reduced, and the sample dimension, n, is kept fixed, then the total number of operations in the calculation is reduced, together with the precision of the measurement. But FIG. 2A shows that, despite the reduction in absolute precision, the precision of calculations using equation (2) improves when the calculations relate to a sample which has been subjected to a measurement using equipment with fewer channels, n, relative to the precision of calculations based on measurements on the same sample using equipment that has a higher dimensionality, n (i.e. that has more measurement channels). Although the absolute precision is less when the number of principal components r, being analyzed is reduced, a system with lower dimensionality, n, is less sensitive to this reduction in the number of calculations, Z, relative to a system with higher dimensionality, n. Thus, a system with lower dimensionality, n, is more versatile and can be better adapted to newer and simpler algorithms and processes. All of this is a powerful motivation for reducing the number of measurement channels, n, in the equipment (and thus in the calculations using information from the equipment based on the measurements) for any given problem where PCA techniques are applied. There is, however, a limit to the degree of reduction in the number, n, of measurement channels to be used by the measurement system. This limit is given by the concept of Entropy Variance, which will be discussed below.

Discretization Technique

Mathematically, the process of discretization can be viewed simply as a summation of matrix components over a certain number, d, of elements. This is described in Eq. (5) below, $$\tilde{C}_{ik} = \sum_{j}^{d} \beta_i \cdot C_{(i \cdot d + j)k} \quad (5)$$

The factor $\beta_i$ is a parameter that needs to be adjusted in the process of optimization, also defined herein as training or calibration of the instrument in question. The dimensionality of the PCA problem is then reduced from n, to n'=n/d, therefore reducing the computational time and the hardware requirements concomitantly. However, an operation such as the one described in Eq. (5) carries the cost of information loss due to reduced precision. On the other hand, as the discretization process takes place, there is a reduction in "graininess" that increases the information content of the reduced data set. The balance between these competing effects can be quantified in different ways; one useful procedure is through the use of the relative entropy matrix (REM)[1]. A variable is defined that quantifies the information content of a given data set. This is called the "entropy of the pooled data set". In the case considered here (PCA analysis), the "pooled" data set is none other than the matrix C. Note that matrix C is built by using carefully selected data sets called principal components. The numbers representing the magnitudes of the principal components in matrix C are known because the samples used to generate the values in matrix C have been carefully prepared with known magnitudes of the principal components. These samples with known magnitudes of principal components are then measured by the same hardware that will be used to measure the magnitudes of the principal components in samples with unknown magnitudes of the same principal components. Therefore, matrix C is directly linked to the hardware of the measurement technique. The entropy is defined as:

[1] I. Lerche; "Some Notes on Entropy Measures", Mathematical Geology, Vol. 19, No. 8 1987.

$$E_n(k) = -\frac{1}{\ln n} \sum_{j=1}^{n} C_{jk} \ln(C_{jk}) \quad (6)$$

By maximizing the entropy, $E_n$, the data set is guaranteed to carry the maximum possible information content[2]. Equation 6 actually refers to a "relative" entropy measure, assuming a maximum normalized value of $E_n(k)=1$. The parameter k is a counting index given by $1 \leq k \leq m$, and m is the total number of different records of data available, which in the case of matrix C would be the total number of principal components to be used. A variance in the average relative entropy, or Entropy Variance, is then defined as:

$$\delta R(n)^2 = \frac{1}{M-1} \cdot \sum_{k=1}^{m} (E_n(k) - \langle E_n(k) \rangle_n)^2 \quad (7)$$

[2] C. E. Shannon; "A Mathematical Theory of Communication", The Bell System Technical Journal, Vol. 27, pp. 379-423, 623-656, July, October, 1948.

Entropy, $E_n$, is not the most convenient parameter to characterize the information content of a given data set. The parameter becomes indeterminate for extreme values of the data size, n, like, n=1, or n approaching infinity. A more convenient criterion, rather than to maximize the entropy, is the minimization of the Entropy Variance, $\delta R(n)$ (Eq. (7)), (Lerche, 1987).

Figure 2B:
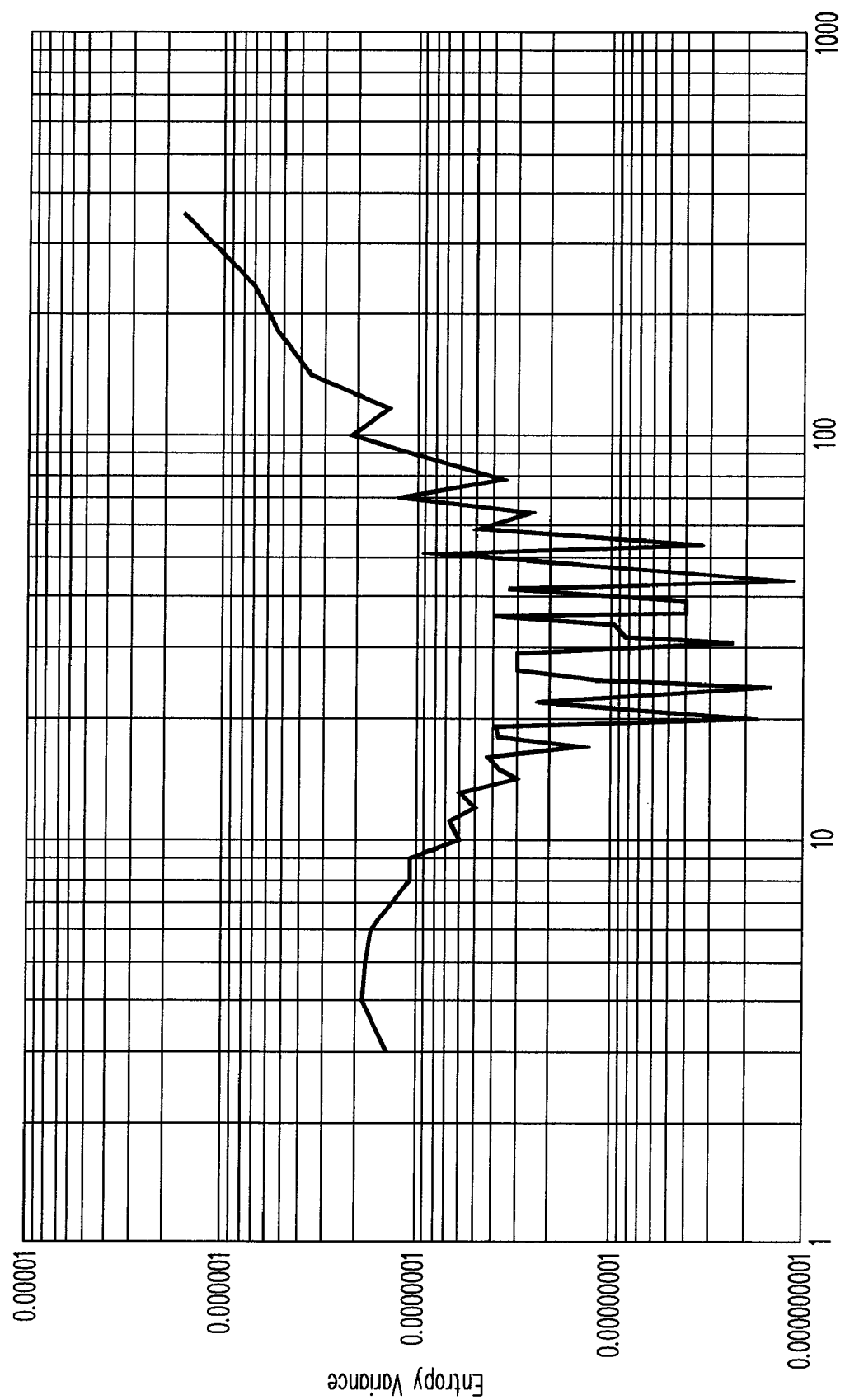

FIG. 2B shows the result of applying the concept of Entropy Variance from Eq. (6) and Eq(7) to the problem of finding the content of cholesterol, collagen and elastin in a given sample, using near infrared spectra and molecular filters to find principal components. FIG. 2B establishes that the optimal number of channels to be considered for that particular problem would be between twenty (20) and sixty (60), for example, about fifty (50). More importantly, FIG. 2B shows that if the number of channels in that particular problem is reduced below twenty (20), then the information content of the channel set quickly deteriorates.

Figure 3:
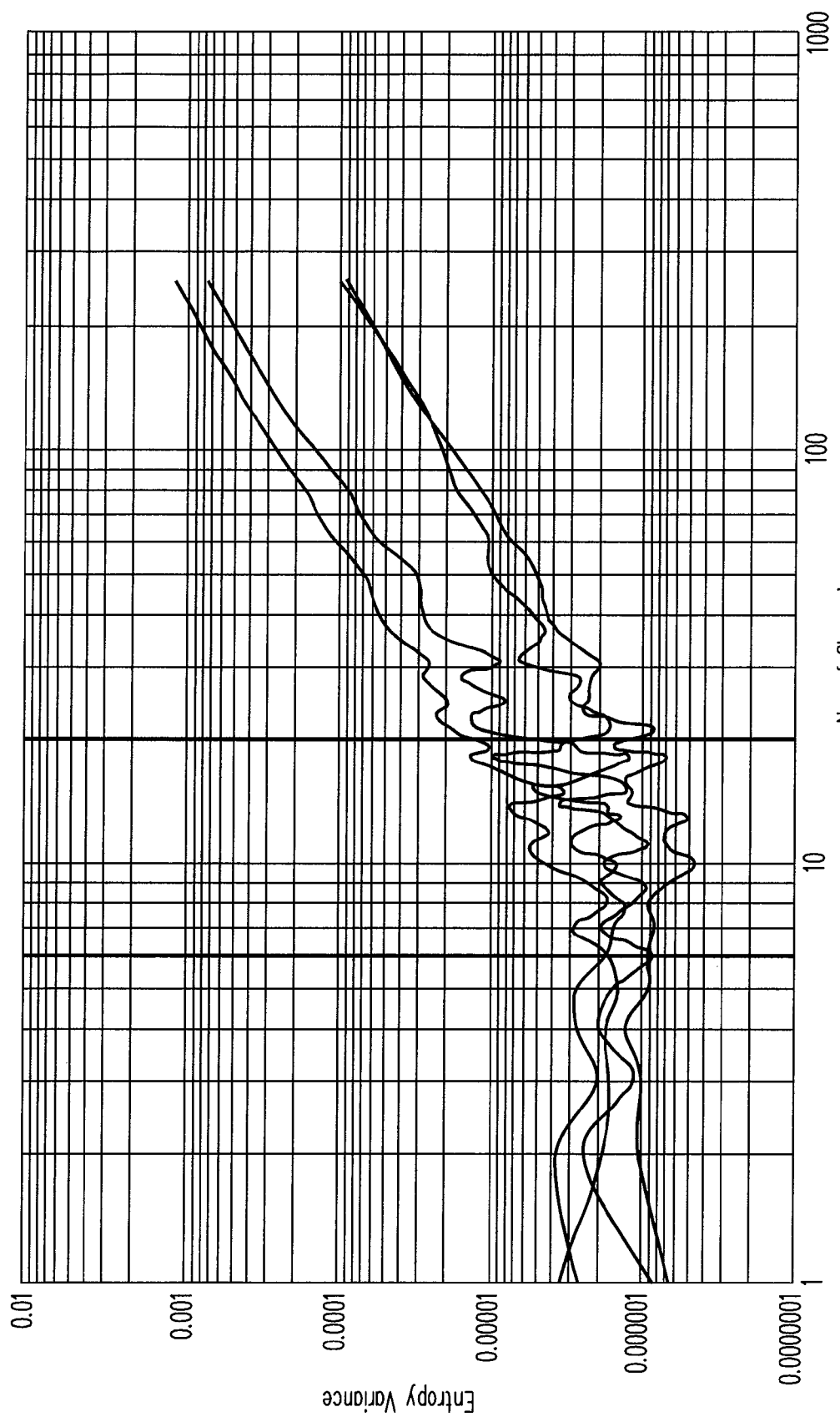
FIG. 3 shows the entropy variance as function of the array size for m sets of NIR spectra of glucose solutions (m=71)
Figure 4:
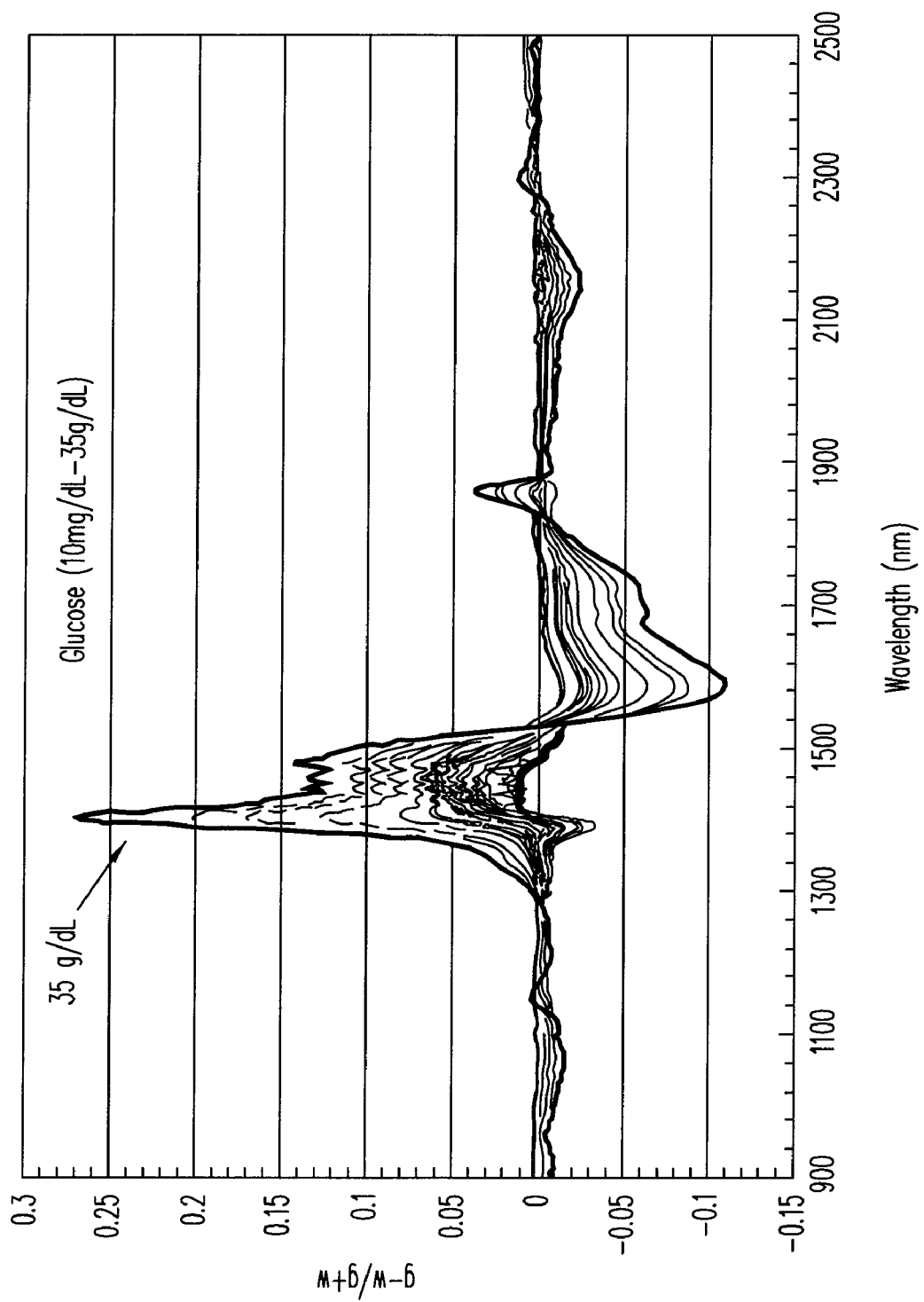
FIG. 4 shows near infrared spectra of glucose and water solutions with varying glucose concentrations from ten (10) milligrams of glucose per deciliter (mg/dL) of water in increments of ten (10) milligrams of glucose per deciliter of water up to five hundred (500) milligrams of glucose per deciliter of water and thereafter in increments of five hundred (500) milligrams of glucose per deciliter of water up to ten (10) grams of glucose per deciliter of water, and thereafter in increments of five thousand (5000) milligrams of glucose per deciliter of Water up to thirty five (35) grams of glucose per deciliter of water.

FIG. 3 shows the result of applying the concept in Eqs. (6) and (7) to determine the number of channels, n, using near-infrared (NIR) spectra to measure the concentration of glucose in water. In this case, the variable, m (Eq. (7)), expresses solutions with different concentrations of glucose. The spectra of the glucose solutions in question are shown in FIG. 4. The spectra consist of arrays, $C_k$, with 256 data points, each point representing a different wavelength in the NIR domain. The data points can be "binned" together (averaged) in sets of different sizes, resulting in a varying number of channels or (bins), into which the data is distributed. As the binned array size is reduced, according to Eq. (5), the variance in the entropy shows a pattern analogous to that of the well-known Allan variance plots[3]. Based on this analysis, the conclusion is that to determine glucose concentration in a water solution by using NIR spectra, collected by exposing the glucose-water sample to NIR radiation filtered to provide information carried by different wavelengths in the 850 nm to 2500 nm wavelength range, the ideal number of data binning (i.e. the number of measurement channels required in the equipment used to measure the concentration of glucose in water) should be somewhere between 6 and 11.

[3] D. W. Allan; "Statistics of Frequency Standards", Proceedings of the IEEE, 54(2) 2213-230 (1966).

FIG. 4 shows near infrared spectra of glucose and water solutions with varying glucose concentrations from ten (10) milligrams of glucose per deciliter (mg/dL) of water up to thirty five (35) grams of glucose per deciliter of water. The spectra were collected using a grating-based spectrometer (from Ocean Optics, Inc. in Dunedin, Fla.) with a two hundred fifty six pixel, indium gallium arsenide photodetector array. Alternatively, the structure shown in FIG. 5C or the structure shown in application Ser. No. 11/452,129 filed Jun. 12, 2006 and entitled "High Speed, Rugged, Time-Resolved, Raman Spectrometer for Sensing Multiple Components of a Sample" assigned to the assignee of this application, can be used as the structure to collect the spectra of the glucose-water samples. application Ser. No. 11/452,129 is incorporated herein by reference in its entirety.

Optimization/Training/Calibration

Figure 5A:
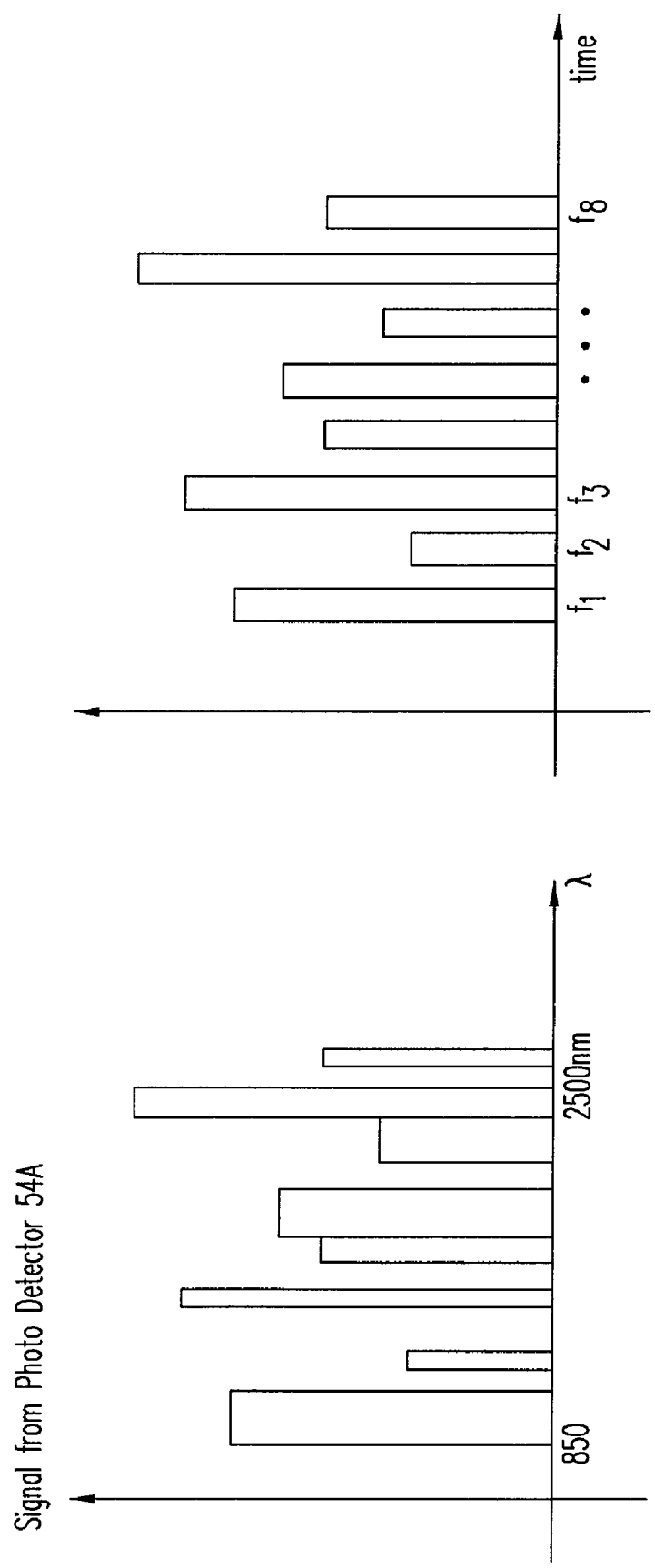
FIGS. 5A and 5B show the signals generated as a function of frequency and time, respectively, by the structure shown in FIG. 5C, which structure is for measuring, as an example of the operation of this invention, the amount of glucose in water.
Figure 5B:
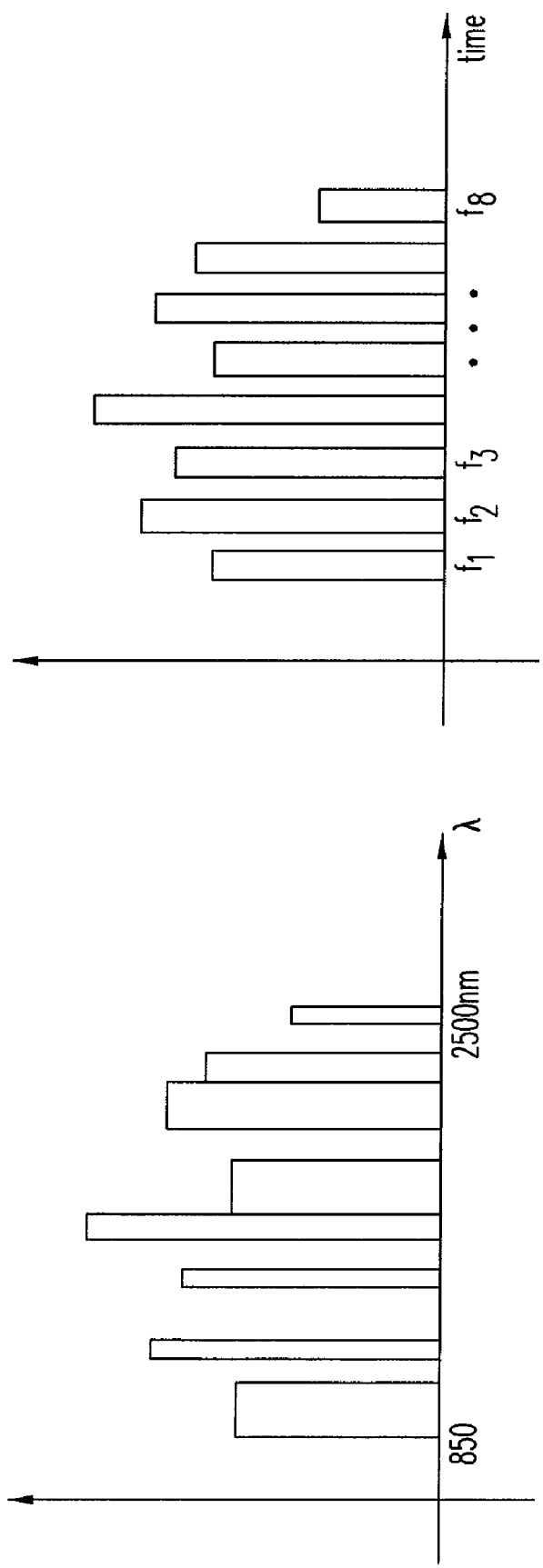
Figures 5C, 6B:
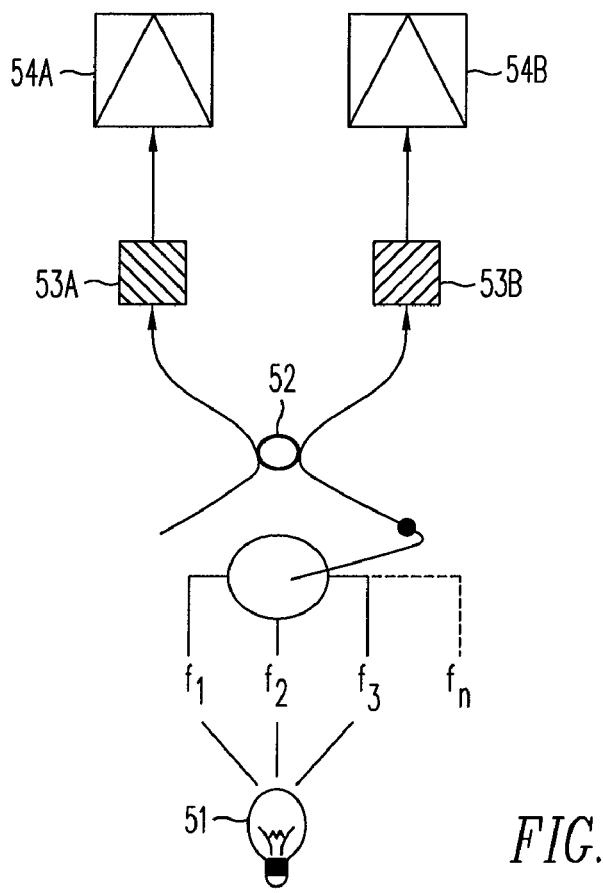
FIGS. 6A and 6B show the center wavelengths, $\lambda_c$ (in nanometers), the bandwidths, $\Delta\lambda$ (in nanometers), and the absorbances, $1-\kappa$, where $\kappa$ is the transmissivity of each filter, of eight interference filters selected for use in the structure of FIG. 5C to measure the amount of glucose in water.

Once it has been established that a data discretization procedure renders more information and at a lower cost for a given problem, the next crucial step of the dPCA technique involves the selection of an optimized set, with a fixed number of discrete data subgroups. Following the example shown in FIG. 3 and FIG. 4, it is decided to use nine (9) different groups of wavelength "averages" across the NIR spectrum, for the measurement of glucose/water solutions. This means nine (9) different channels (i.e. "n" equals nine (9)) will be used in the measuring equipment. The architecture of the glucose sensor is shown in FIGS. 5A, 5B and 5C, except FIGS. 5A, 5B and 5C relate to a system with eight (8) filters, while actually nine (9) filters were used in the system depicted schematically in FIG. 5C instead of eight (8) filters. Eight (8) of the filters have characteristics as shown in FIG. 6B, while the ninth filter had a center wavelength, $\lambda_c$ of 1683 nm, a bandwidth, $\Delta\lambda$, of 50 nm, and a transmissivity of 0.7. FIG. 5C shows lamp 51 which produces light which passes in sequence through filters f1, f2, f3, to fn, where n is a selected integer equal to eight (8) in FIG. 5C but equal to nine (9) in the actual system used to run the experiments reported here. Light source 51, shown schematically in FIG. 5C as a light bulb 51 actually is a rotating light source of the type shown in FIGS. 1A and 1B, for example, of co-pending application Ser. No. 11/603,939 filed Nov. 21, 2006 and assigned to the assignee of this application. Application Ser. No. 11/603,939 is hereby incorporated by reference herein in its entirety.

In one embodiment, as discussed above, the number of measurement channels n is eight (8), meaning that eight (8) different filters are used. The light from each filter is sent through beam splitter 52 (which splits the light 50/50) and the separate split beams of the light are then sent through a sample of a glucose and water mixture, held in container 53A and a sample of pure water held in container 53B to photodetectors 54A and 54B, respectively.

Photodetector 54A produces a signal representative of the amount of glucose in water while photodetector 54B produces a signal representative of pure water. FIG. 5A represents an illustrative (not the results of actual experiments) spectral sequence (i.e. the signal amplitude as a function of wavelength) in the left graph as could be detected by photodetector 54A and the corresponding illustrative time sequence of the signals from filters f1 to f8 as could be detected by photodetector 54A in the plot on the right. The various amplitudes depicted in these plots show the transmission efficiency of the combination of the water-glucose mixture in container 53A and each filter, in time sequence. Each filter f1 to f8 is part of a unique channel. Each channel comprises the light that passes through the filter and the water-glucose combination to be incident upon the photodetector 54A together with the mathematical operations to be conducted on the resulting signal from photodetector 54A. The channel will also include any hardware or physical structure arranged to further process the light that passes through the corresponding filter or that further processes the signal from photodetector 54A in response to such light. For example electronic or optical processing (such as attenuation or amplification) of either the optical or the electrical signal traveling through the channel is also part of the channel.

Photodetector 54B produces a signal representative of the pure water. FIG. 5B represents the illustrative (not the results of actual experiments) spectral sequence (i.e. the signal amplitude as a function of wavelength) in the left graph as could be detected by photodetector 54B and the time sequence of the signals from filters f1 to f8 as could be detected by photodetector 54B in the plot on the right. The various amplitudes shown in these plots show the transmission efficiency of the combination of the pure water in container 53B and each filter, in time sequence. As stated above, each filter f1 to f8 is part of a unique channel. Each channel comprises the light that passes through the filter and the pure water to be incident upon the photodetector 54B, together with the mathematical operations to be conducted on the resulting signal from photodetector 54B. The channel will also include any hardware or physical structure arranged to further process the light that passes through the corresponding filter or that further processes the signal from photodetector 54B. For example electronic or optical processing (such as attenuation or amplification) of either the optical or the electrical signal traveling through the channel is also part of the channel.

This invention uses the signals shown in FIGS. 5A and 5B which are generated by the structure in FIG. 5C as inputs to the unique algorithm which is called herein discrete principal component analysis. This novel analysis algorithm allows the data generated by the structure shown in FIG. 5C to be analyzed rapidly in a real-time manner and in other than a laboratory environment.

It is useful to define a new variable S as in equation (8) below.

$$S = \sqrt{\sum_i (1 - \kappa_i \cdot (A_i - B_i)/(A_i + B_i))^2} \tag{8}$$

In equation (8), $A_i$ is the signal in $f_i$ related to the sample (e.g. a given concentration of glucose in pure water solution) and $B_i$ is the signal in $f_i$ related to a reference sample (e.g. pure water). The glucose concentration, [g], is obtained from S by a linear expression, $$[g] = K_g \cdot S + b \tag{9}$$

In equation (9), $K_g$ and b are correlation constants. Equation (9) expresses [g] as a nonlinear function of the signal measured from the sample, $\vec{A}^t \approx (A_1, A_2, \ldots, A_n)$. This clearly contradicts the basic assumption of PCA, as stated in Eq. (1). However, it is well known that under low glucose concentration conditions, $\vec{A} \approx \vec{B}$, so Eq. (8) can be approximated as, $$S \approx \sqrt{n} \cdot \left(1 + \frac{\vec{B}^T \cdot \vec{v}}{2} - \frac{\vec{A}^T \cdot \vec{v}}{2}\right) \tag{10}$$

In equation (10) the vector, $\vec{v}$, is given by $$\vec{v}^t = (\kappa_1/B_1, \kappa_2/B_2, \ldots, \kappa_n/B_n) \tag{11}$$

Making the following associations, $$b = -K_g \cdot \sqrt{n}, \tag{12.1}$$

$$(C^t \cdot C)^{-1} \cdot C^t = \frac{K_g}{2} [\vec{v}^t], \tag{12.2}$$

$$P = [\vec{B} - \vec{A}], \tag{12.3}$$

$$R = [g]. \tag{12.4}$$

it turns out that Eq. (9) can be written for R=[g] as, $$R = (C^T \cdot C)^{-1} \cdot C^T \cdot P \tag{13}$$

Furthermore, matrix C, which in this case is a vector corresponding to the only principal component in the problem, can be extracted from Eq. (12.2), to be found as $$C = \left(\frac{2}{K_g}\right) \cdot (\vec{v} \cdot \vec{v}^t)^{-1} \cdot [\vec{v}] \tag{14}$$

In essence, the dPCA procedure here comprises finding the values of $(f_i, \delta f_i, \kappa_i)$ such that the linearity in Eq. (9) is satisfied, and such that the error (variance) in the measurement, $\sigma_{max}$, is minimized. This is equivalent to finding suitable values of $\beta_1$ in Eq. (5).

Note that in principle the data sets do not need to be continuous in the wavelength domain. A detailed description of one application of this technique follows. The architecture of the device in FIG. 5C makes use of interference filters and homogeneous integration of the signal across the filter bandwidth, using a single photodetector. Before measuring the signals generated by each glucose-water sample using a structure such as shown in FIG. 5C, theoretical calculations of the signals expected from the structure shown in FIG. 5C were made assuming that each of the eight (8) filters in the structure of FIG. 5C had the values shown in FIG. 6B. The actual experiments run on the glucose-water samples discussed above used the structure shown in FIG. 5C but modified this structure to include a ninth channel with a filter having the characteristics described above as the ninth filter. In the actual experiments, all nine (9) interference filters were selected to maximize the measurement accuracy for a glucose solution in water.

Figure 6A:
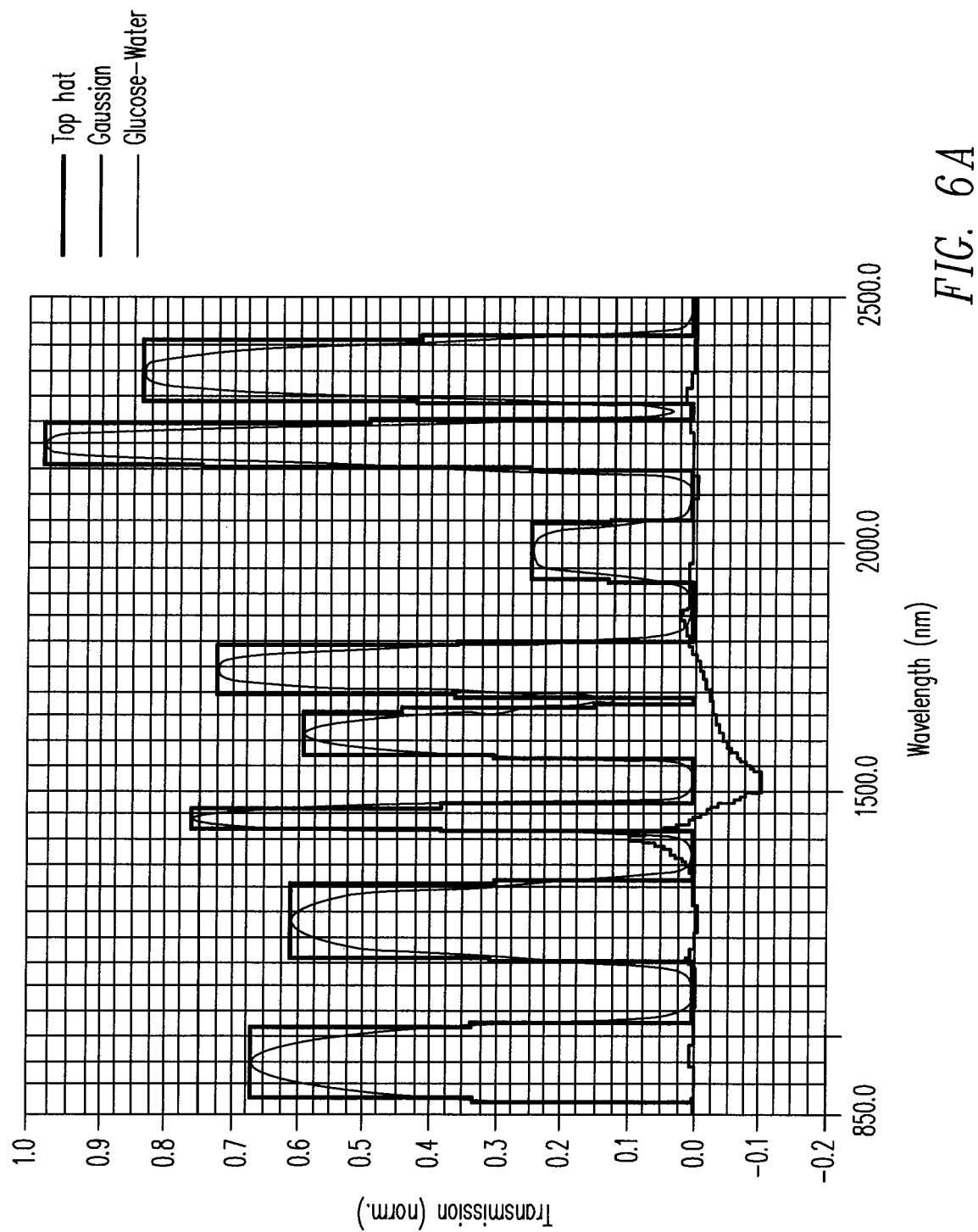

FIGS. 6A and 6B depict a particular set of eight (8) filters used in theoretical calculations to determine a theoretical matrix C, with the vertical rectangles in FIG. 6A defining each filter's pass band. The spectral signature of the glucose signal relative to water (i.e. the curve crossing from one side to the other of the graph in FIG. 6A) is overlaid in FIG. 6A to emphasize the role of the "relevant features" in the filter selection. The spectroscopic data used for the calculations is shown in FIG. 4.

Figure 7A:
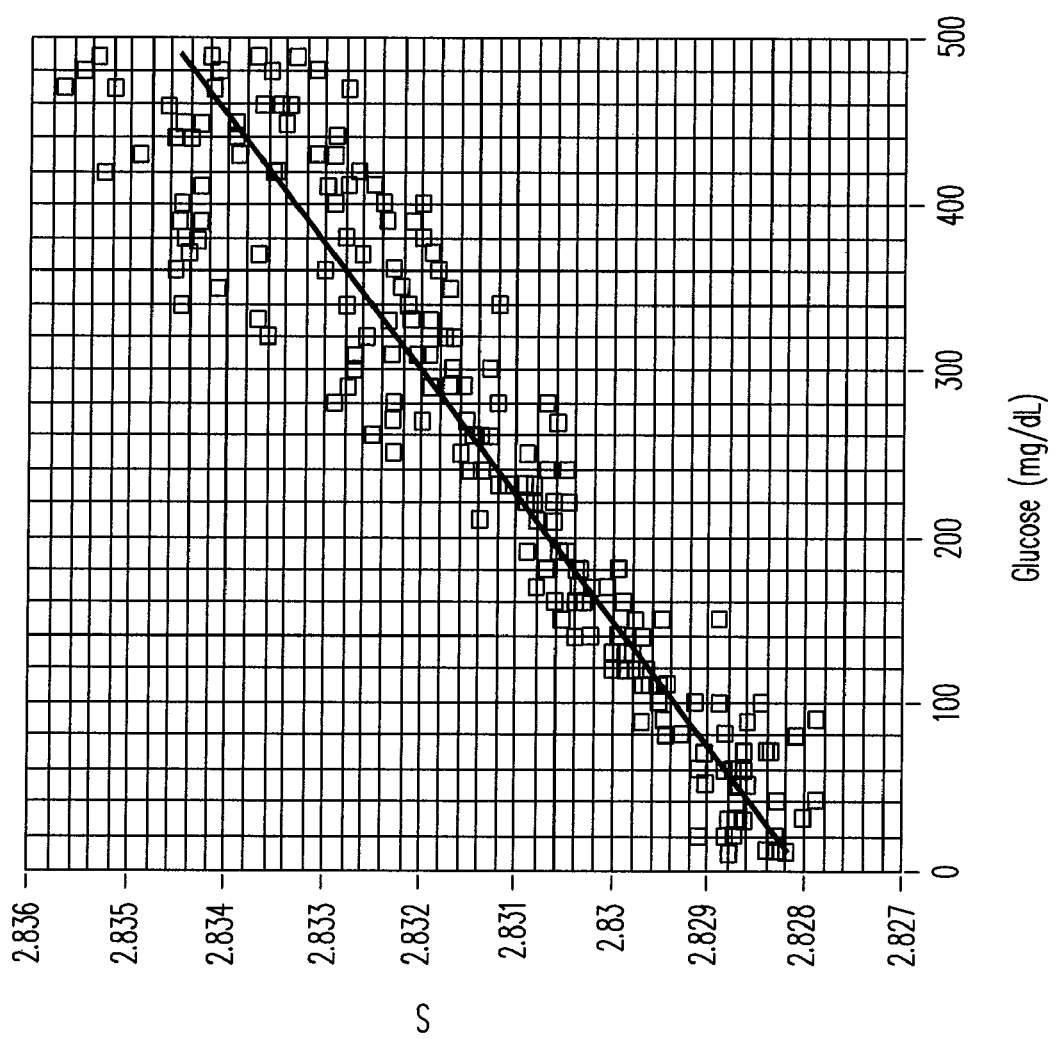
FIGS. 7A and 7B show the results of the discrete Principal Component Analysis optimization procedure in accordance with this invention, in terms of a linear correlation between the parameter S and glucose concentration of the samples.
Figure 7B:
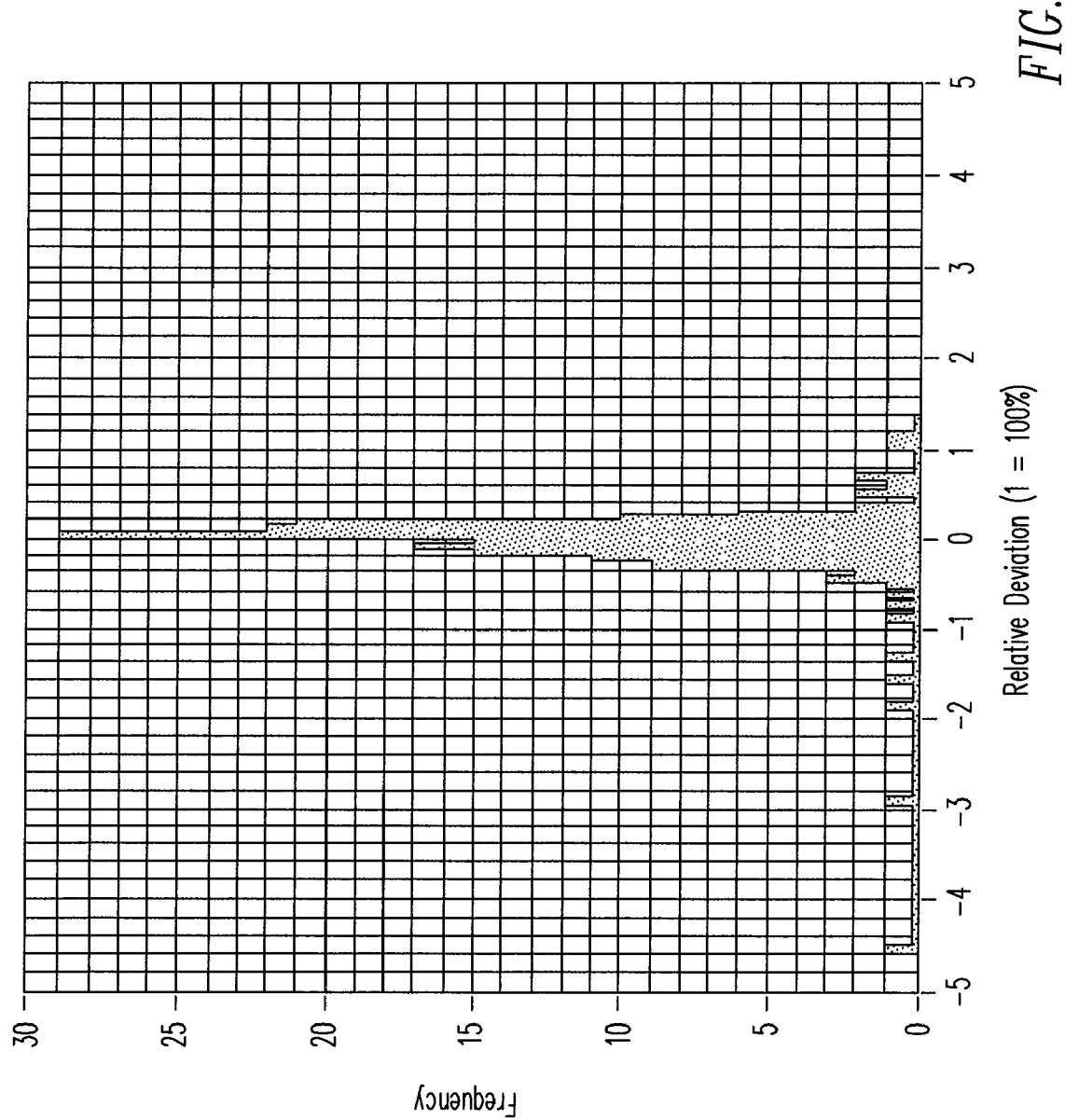

The theoretical calculations used to obtain an optimized set of eight (8) filters involve the use of a stochastic scan of the 24-dimensional parameter space that spans all possible sets of eight (8) interference filters, each with a given bandwidth, transmission, and center wavelength ($\Delta\lambda_c, \tau, \lambda_c$). Using a statistically significant set of sample spectra, with glucose concentrations ranging from 10 mg/dL up to 500 mg/dL (FIG. 4), the optimization routine (using trial and error calculations) selects the filter set that minimizes the relative variance in the data. The result of the optimization routine is shown in FIGS. 7A and 7B, where a linear correlation is found between a suitable variable, S, and the glucose concentration of the solution, [g]. The variable S is a combination of operations performed on the "discretized", 8-dimensional signal produced by the light detected through the eight (8) interference filters, using a single photodetector as shown in FIG. 5C. To generate the data in FIG. 7A, the data from the first fifty samples of glucose in water used to generate FIG. 3 and FIG. 4 was further utilized. In each subset of fifty (50) samples from the four (4) sets, each of seventy one (71) samples used to generate FIG. 3 and FIG. 4, each sample increased by 10 mg/dL in concentration from the previous sample. The samples ranged from 10 mg/dL to 500 mg/dL glucose in water. Thus two hundred (200) data points are shown in FIG. 7A. The data used to obtain FIGS. 7A and 7B is thus a subset of the data used to prepare FIG. 3 and FIG. 4 and was obtained using the grating-based spectrometer described above.

Figure 8A:
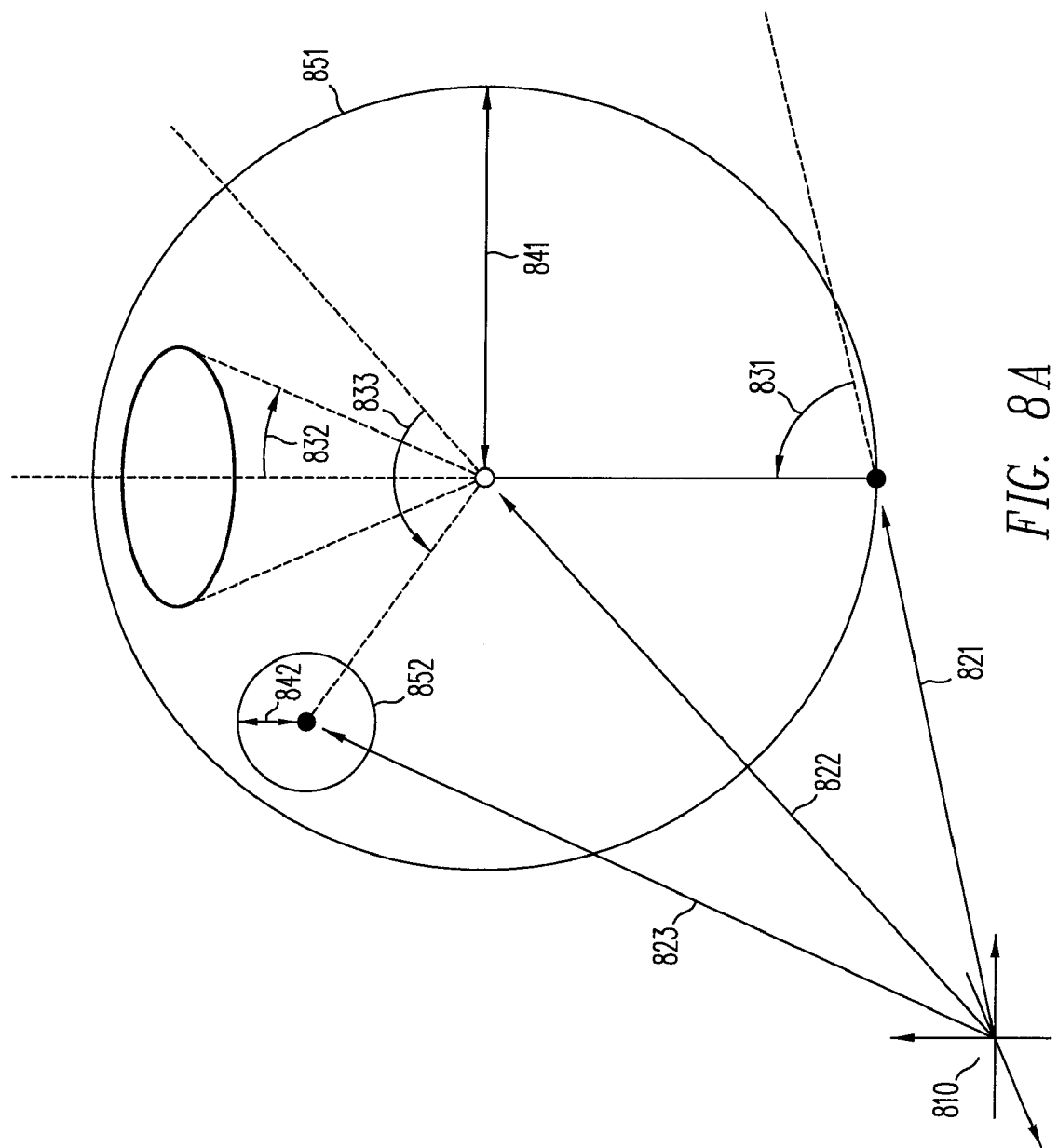
FIGS. 8A, 8B and 8C show the principle of construction for the stochastic trajectory through the parameter space, in order to maximize the determinant, $\text{Det}(\bar{\xi})$. The parameter space, $Q^L$, is an $L=f\otimes n$ dimensional space, where f is the number of features that describe completely a single measurement channel, and n is the number of channels to be considered in the measurement. The process is a doubly-iterative sequence.
Figure 8B:
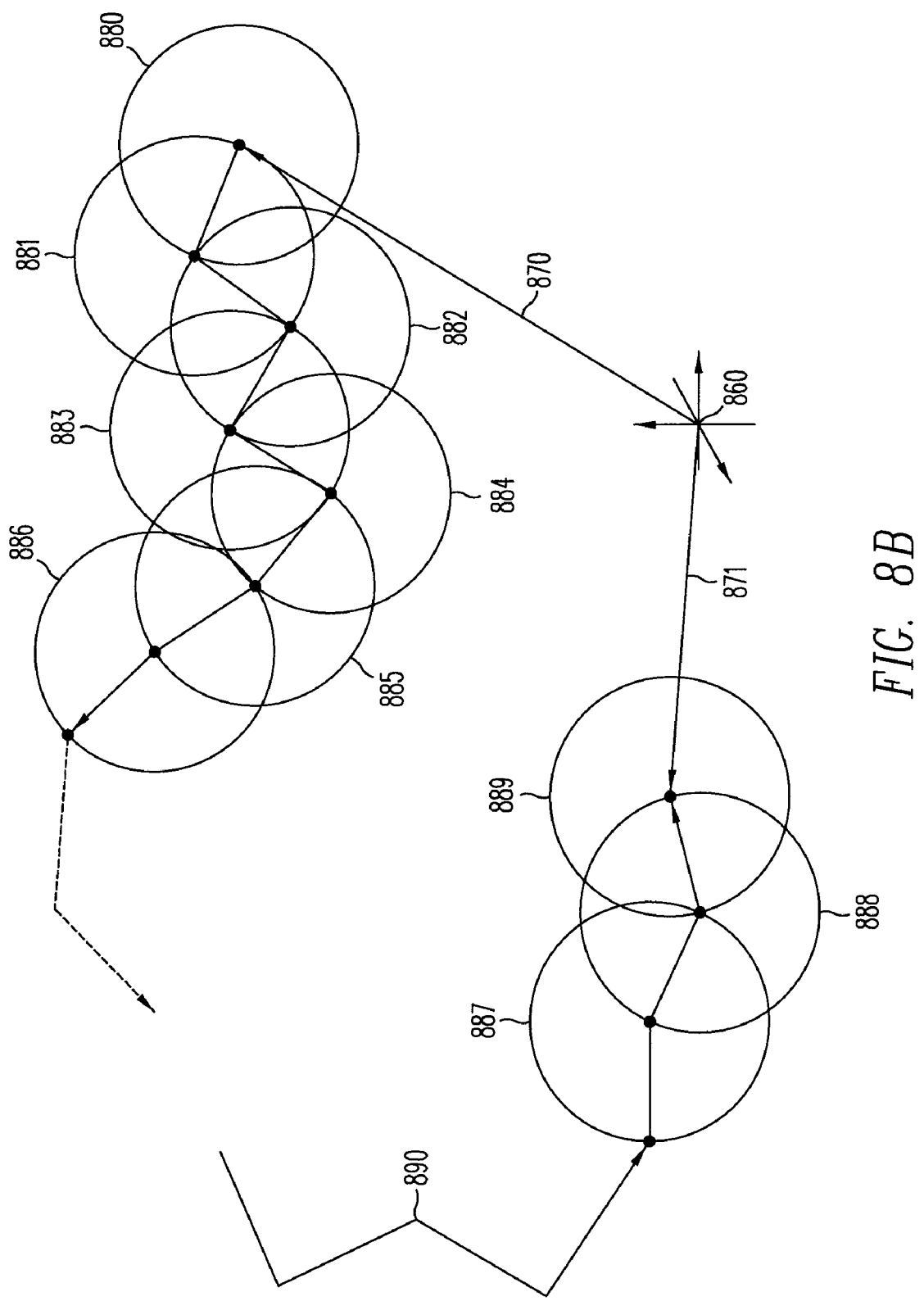

The stochastic parameter scan used to optimize the performance of the discretized channel set is described schematically in FIG. 8A and FIG. 8B. Each channel set of size, n, is associated with a point in the L-dimensional set of points, $Q^L$, which is a subset of, $R^L$, the Euclidean space of dimension, $L=f \otimes n$, where f is the number of characteristics associated with a single channel. The optimization consists in scanning $Q^L$ to find the point such that the determinant of matrix, $\xi$, defined in Eq. (2), is maximized. The point thus selected will represent the characteristics of a channel set of size, n, that maximizes the performance of the measurement device. In the specific case of the measurement of glucose in water using n=8 channels, corresponding to spectroscopic filters each with three characteristics (i.e. f=3 corresponding to filter bandwidth, $(\Delta \lambda_c)$, transmissivity $(\tau)$, and center frequency wavelength $(\lambda_c)$), the set $Q^L$ has dimension, L=24. The parameter point, $\vec{r}_i$, is therefore a group of twenty four (24) numbers that completely define a set of eight filters used to measure glucose concentrations in water. Notice that the geometry of the set $Q^L \subset R^L$, (where the symbol, $\subset$, denotes the concept of "subset") is determined by the physical constraints for the channels in the actual instrument. In the specific case of the measurement of glucose in water using, n=8, channels, corresponding to spectroscopic filters, each point in $Q^L$ is given by the following set of 24 numbers, $\{(\Delta \lambda^1 c, \tau^1, \lambda^1_c), \ldots, (\Delta \lambda^8_c, \tau^8, \lambda^8 c)\}$. These 24 numbers are subjected to the following physical constraints: Sensitivity of the photodetector in the NIR range: 1000 nm$<\lambda^i \pm (\Delta \lambda^i/2)<$2500 nm, for all channels, i=1, ..., 8; bandwidth: $\Delta \lambda^i > 0$, for i=1, ..., 8; non-overlapping of the spectral range amongst all filters: $\lambda^i + (\Delta \lambda^i/2) \leq \lambda^{i+1} - (\Delta \lambda^{i=1}/2)$, for i=1, ..., 7. Anyone skilled in the art would recognize that these constraints can be different in the case of other physical realizations of the optical channels in the system. For example, if the spectral range of sensitivity of the photodetector used is in the UV-visible range: (300 nm, 750 nm), then the constraint would be 300 nm$<\lambda^i \pm (\Delta \lambda^i/2)<$750 nm, for i=1, ..., 8.

Figure 8C:
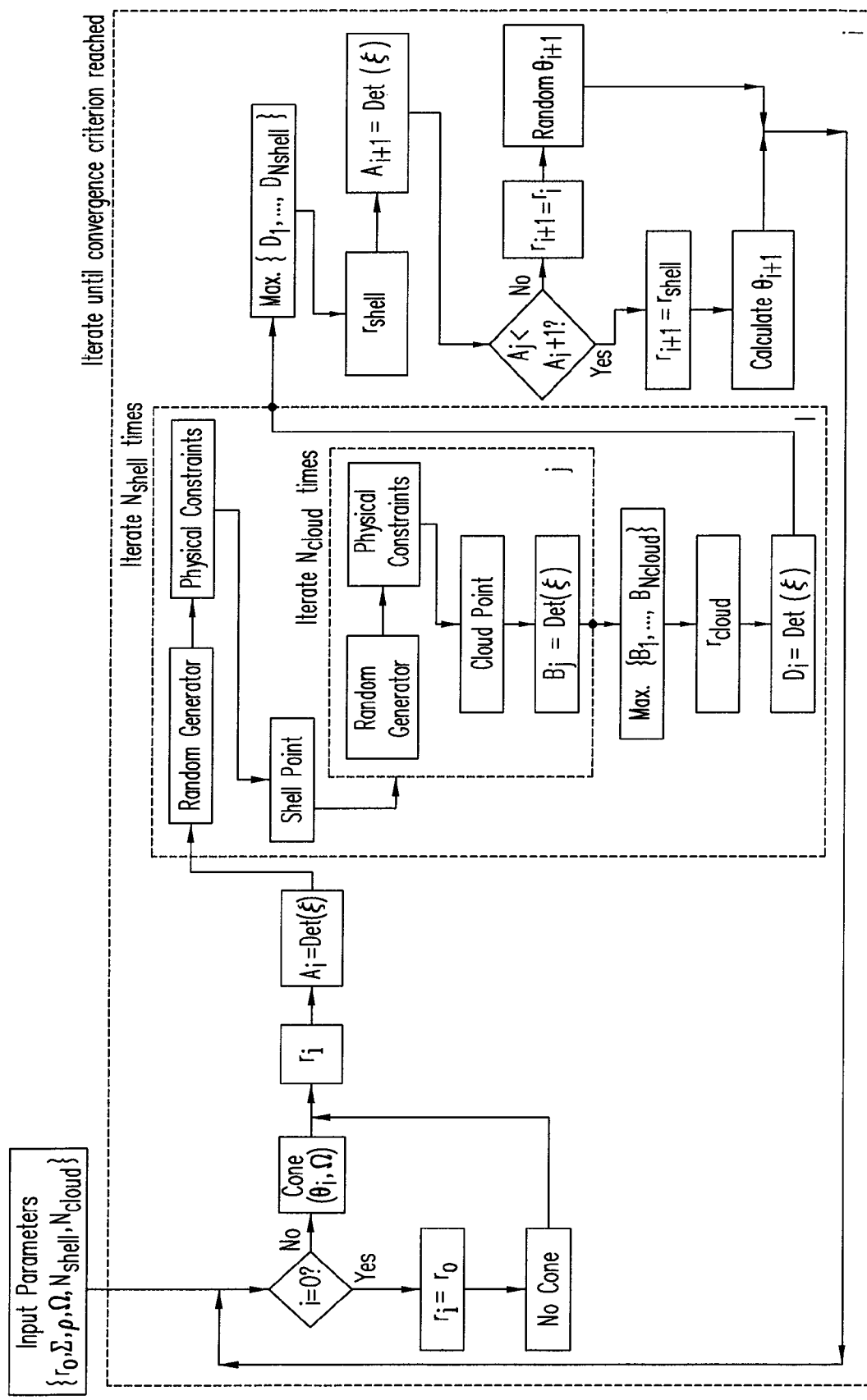

The procedure to scan the set QL consists in the use of a two-step scan, as illustrated in FIG. 8A. In the first step, called the "shell-scan", a number of points, $N_{shell}$, are randomly selected around an initial parameter point, $\vec{r}_i$ 822, within a sphere of a fixed radius, $\Sigma$ 841, centered at $\vec{r}_i$. This sphere will be herein referred to as a "shell" 851. The "shell-points" selected follow a normal distribution of directions around the center point, $\vec{r}_i$ 822. This normal distribution has a fixed angular width $\Omega$ 832 around a specific direction $\theta_i$ 831. The direction $\theta_i$ 831, is selected as the angle formed between vectors and $\vec{r}_i - \vec{r}_{i-1}$ and $\vec{r}_i$. The vector, $\vec{r}_{i-1}$ 821 is the center of the "shell" used in the previous iteration of the routine. For each of the shell points selected, the second step is called the "cloud-scan". This consists on the selection of a new set of $N_{cloud}$ points in QL, clustered around each of the shell points, within a sphere of fixed radius $\rho$ 842. This sphere will be herein referred to as a "cloud" 852. The best mode of operation for the procedure is the radius of the cloud to be less than the radius of the shell, and preferable preferably much less. The points within a cloud are selected randomly, but uniformly distributed around each of the shell points. The first level of computation consists in selecting, for each shell point, the point within the corresponding cloud that maximizes Det($\xi$) labeled $\vec{r}_{cloud}$ in FIG. 8C. Then, the point that maximizes Det($\xi$) amongst all the different clouds within a shell, is selected (labeled $\vec{r}_{shell}$ in FIG. 8C). This point in parameter space will become point $\vec{r}_{i+1}$ 823. Finally, the direction formed between vectors, $\vec{r}_{i+1} - \vec{r}_i$ and, $\vec{r}_i$, is selected as $\theta_{i+1}$ 833, and the process can be repeated a number of times, P, until Det($\xi$) converges to a maximum value.

FIG. 8B shows the final trajectory of the optimization routine in the set $Q^L$. The starting point is shown as $\vec{r}_0$ 870 and the final point is $\vec{r}_P$ 871. For the starting point in the iteration sequence 870, no cone of fixed angular width $\Omega$ can be used to select the shell points. The initial step consists in the choice of starting parameters $\vec{r}_0$, $\Sigma$, $\rho$, $\Omega$, $N_{shell}$, and $N_{cloud}$ all as defined above.

Therefore, in the first step the shell points are equally distributed within the first shell. The shells used in the calculation are also depicted (880 to 889). A fragment of the resulting trajectory is shown 890.

Figure 9:
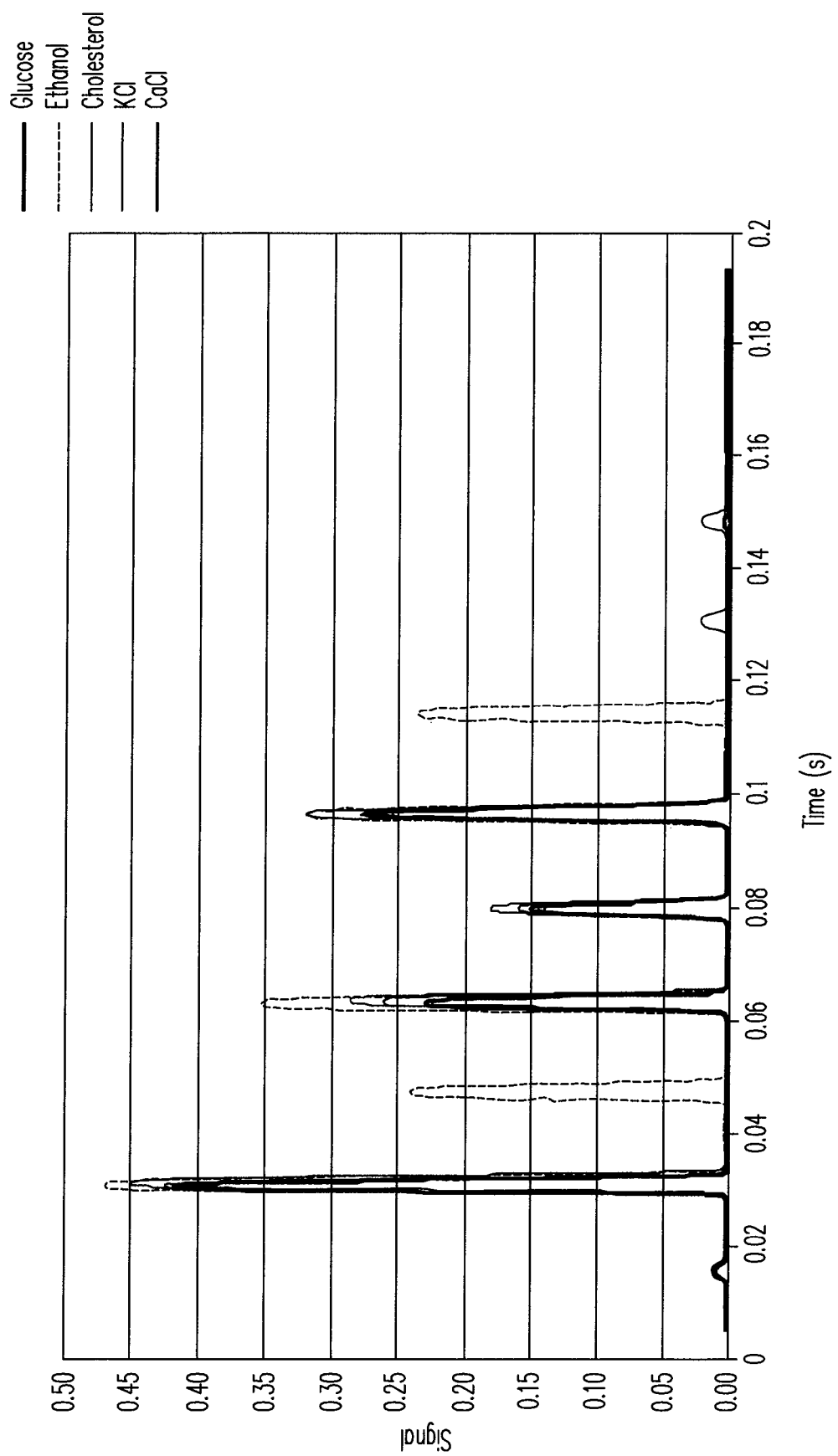
FIG. 9 shows the time sequence of signals from nine channels representing the photodetector output signals as a function of time from five different samples consisting of: (i) a mixture of 35 g of glucose per deciliter of water, (ii) pure ethanol, (iii) a mixture of one hundred (100) milligrams of cholesterol per deciliter of water, (iv) a mixture of one (1) gram of potassium chloride per deciliter of water, (v) and a mixture of one (1) gram of calcium chloride per deciliter of water.
Figure 10:
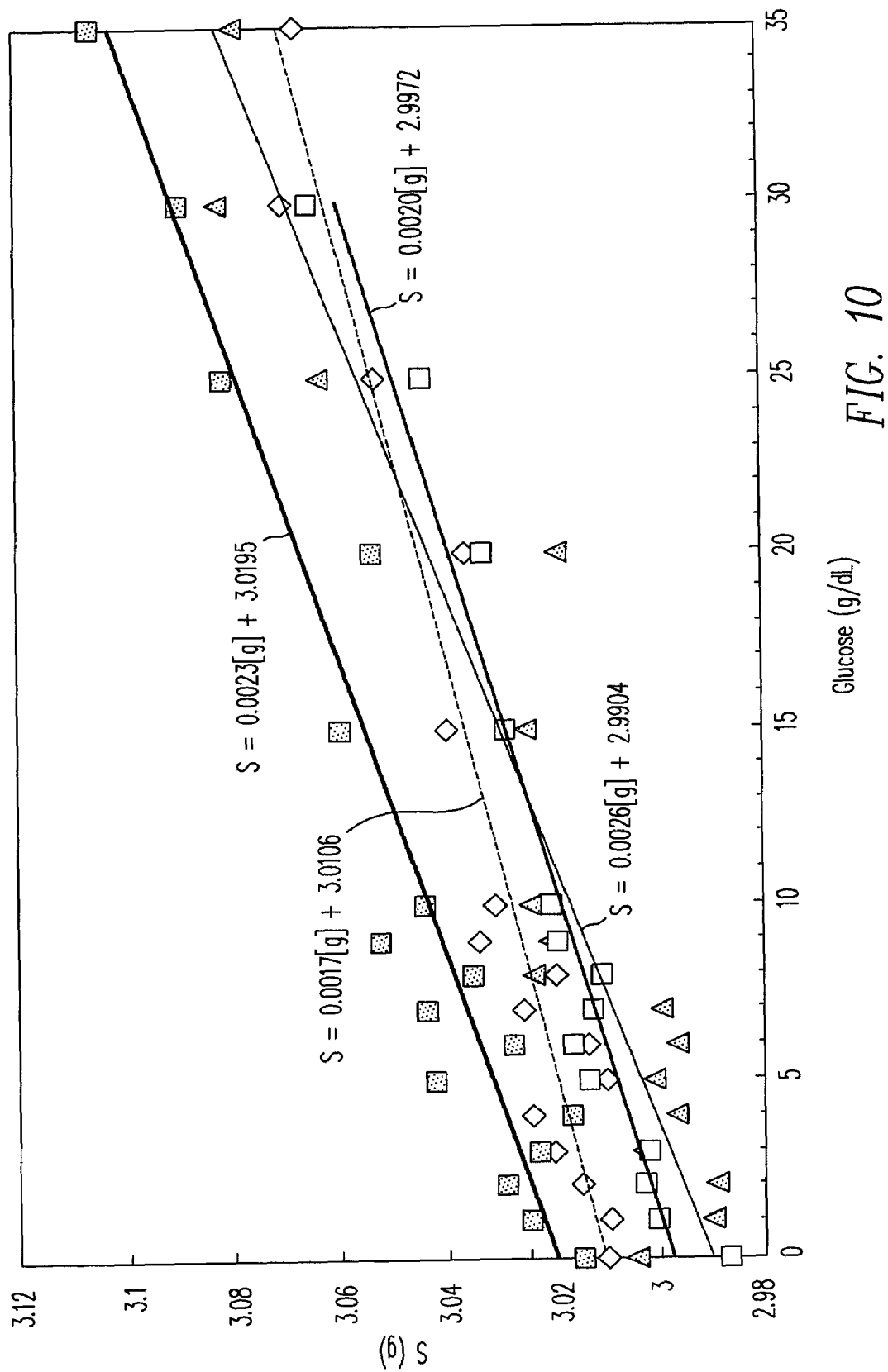
FIG. 10 shows the correlation of S(g) to the concentration of glucose in water where S is as defined in Equation (8) and where the data used was obtained using an instrument as shown in FIG. 5C.
Figure 11:
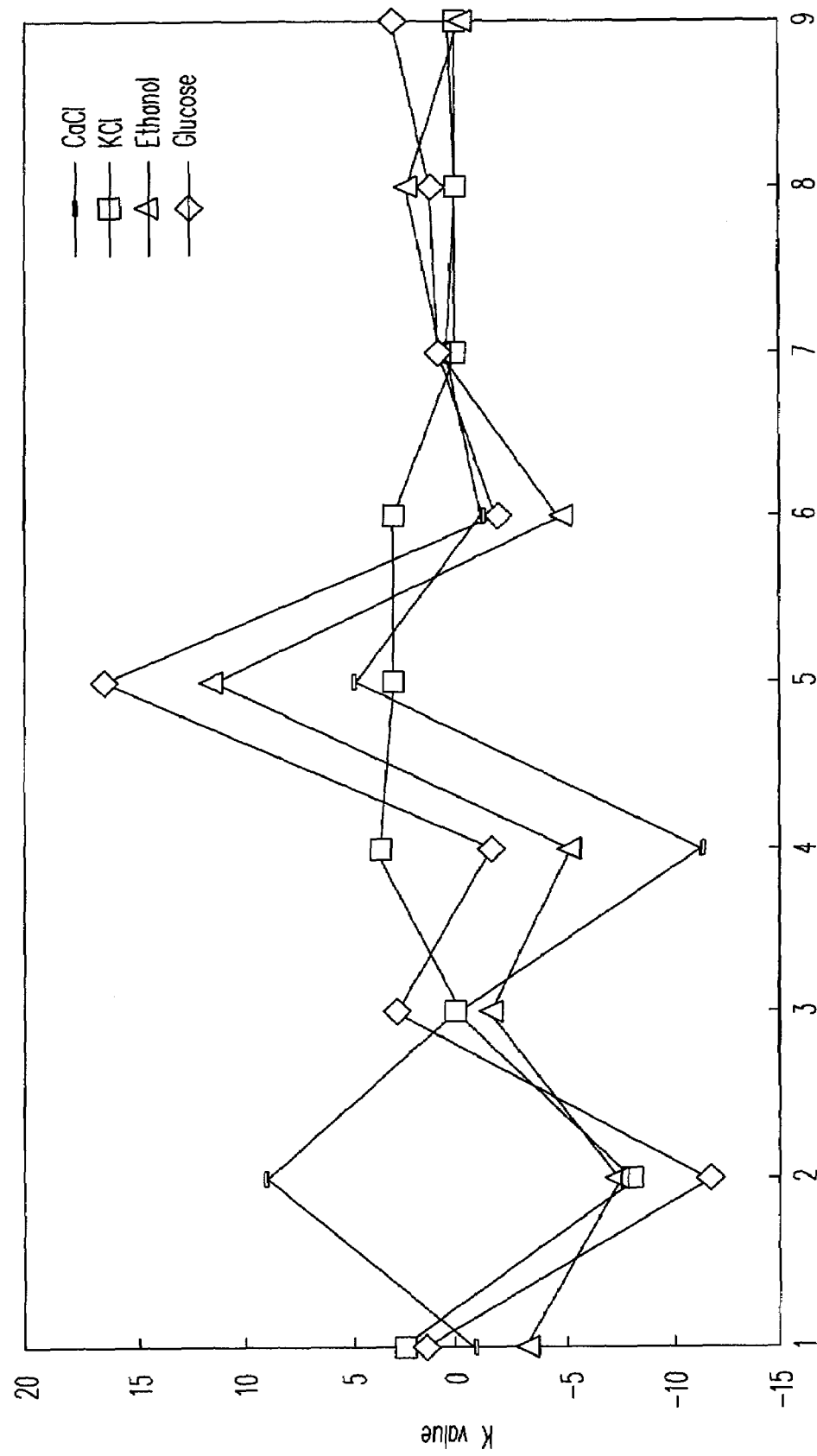
FIG. 11 shows the measured values associated with nine (9) filters used in a structure as shown in FIG. 5C to measure the concentration of glucose in water (the line with diamonds) and also, for illustrative purpose, the concentrations of calcium chloride (line with rectangles) in water, potassium chloride (line with squares) in water and alcohol (ethanol) (line with triangles) in water.

One realization of the device architecture and dPCA algorithm that was described in the previous paragraphs is illustrated in FIGS. 9, 10 and 11. FIG. 9 shows the time-trace of the signal measured by a device as shown in FIG. 5C but with nine (9) channels. The ninth channel having a filter with characteristics as described as described above. The device was operating at 300 RPM. The traces correspond to five (5) different solutions, including glucose, all of them of relevance for biomedical applications. The instrument in question, although similar to the instrument described in FIG. 5C, uses 9 auxiliary channels with nine (9) interference filters spanning a wavelength range in the NIR domain from 1.0 to 2.4 microns. FIG. 10 shows the S([g]) correlation curves obtained for one set of glucose-water solutions (using different samples than the samples used to generate FIGS. 3, 4, 7A, and 7B) measured on four different occasions, in a random sequence. The reason for the difference between the correlations shown in FIG. 10 and the theoretical correlation obtained in FIG. 7A is the fact that the bandpass filters used in the realization of the instrument do not match perfectly the bandpass filters specified by the stochastic method (shown in FIG. 6A and in FIG. 6B) and used in the theoretical calculations that generated FIGS. 7A and 7B. The linear nature of FIG. 10 proves the validity of principal component analysis when used with the simplified equipment shown in FIG. 5C, modified to include a ninth ($9^{th}$) channel as discussed above for the measurement of glucose in water. FIG. 11 shows the resulting vectors for four (4) of the five (5) different solutions (including water) depicted in FIG. 9 (namely CaCl, KCl, ethanol and glucose). The techniques described above are particularly useful for measuring the concentration of glucose in blood, a measurement important in connection with the control and treatment of diabetic individuals. This invention makes possible such measurements in a more economical and rapid manner than previously possible.

Another application of the dPCA technique would be in the field of image processing and pattern recognition. For example, in one application the object of analysis constitutes a 2-dimensional field of points that form the pixilated image of a given object. This data set can be retrieved by any optical means, which may include, but is not limited to, a CCD/CMOS camera or a bundle of optical fibers attached to a scanner head. Also, the information stored in each pixel can have analog or digital format, and can be related to multi-wavelength content, state of polarization of light, intensity of light, and/or phase of electromagnetic field. In this configuration, the role of the dPCA technique is to group together the pixel information, as in Eq. (5), and apply a "measure" operation to the reduced data set that allows for a simple identification of the objects contained in the field of view.

Figure 12A:
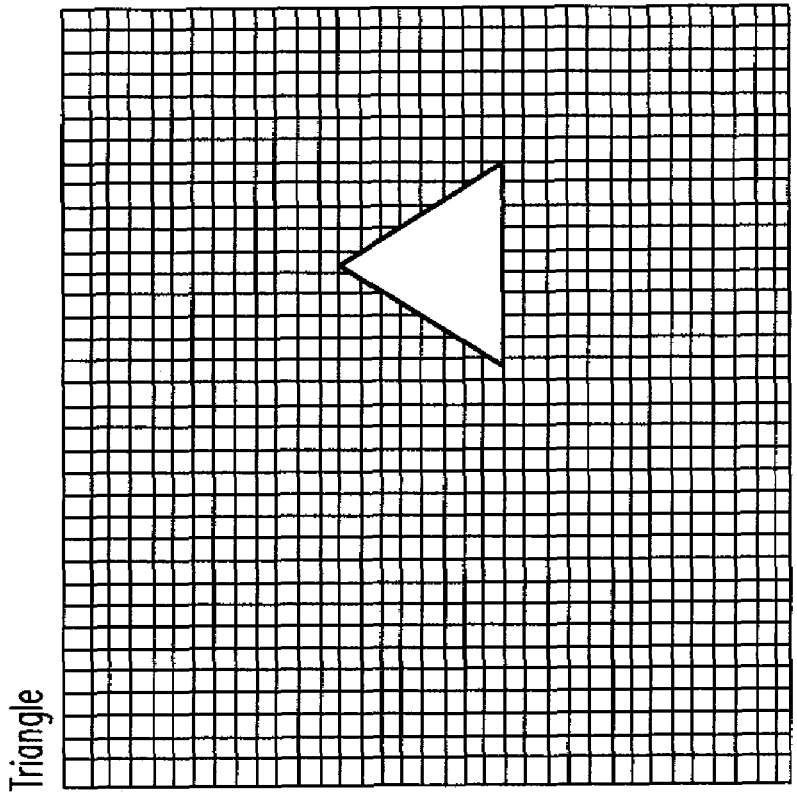
FIGS. 12A and 12B show the ability of the structures and methods in accordance with this invention to recognize different shapes as a function of the number of pixels used in the measurement process.
Figure 12A:
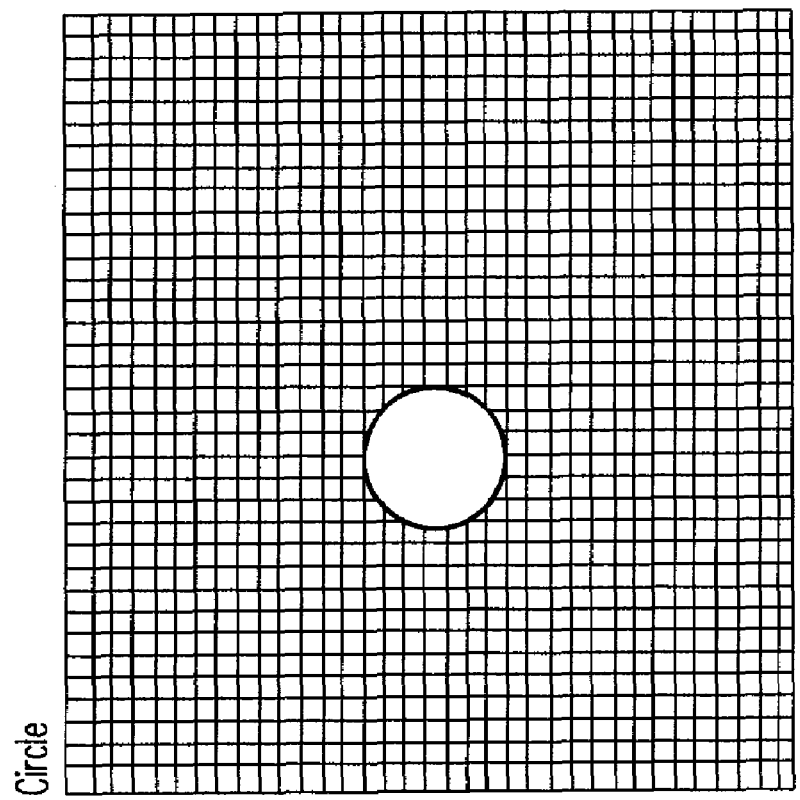
Figure 12B:
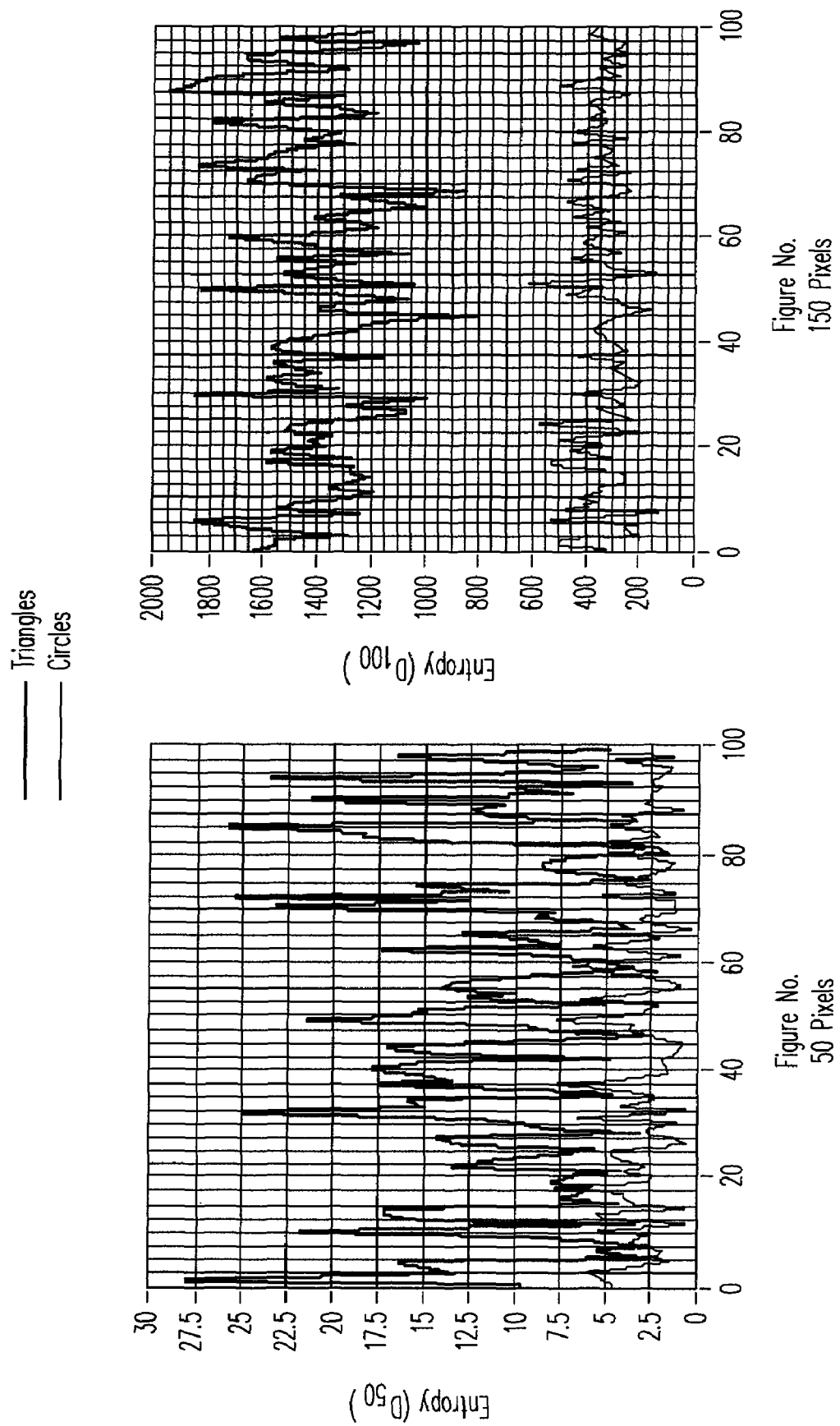

FIGS. 12A and 12B illustrate an example of such a technique. The process consists in the identification of a single object within a 200×200 pixel frame that has a neutral background (grey). The objects in question are a circle and a triangle, of the same area and color, but located at an arbitrary position within the frame, and in the case of the triangles, with an arbitrary orientation. The field of view is then subdivided into an even number of "pixels" on each axis (without loss of generality: $n_x=n_y=n$). For a given number of pixels in the image, $n^2$, a discriminator is defined as $$D_n = \frac{1}{n^2} \sum_i \left( \sum_j \tilde{C}_{ij} \cdot \ln(\tilde{C}_{ij}) \right)^2 \otimes \sum_j \left( \sum_i \tilde{C}_{ij} \cdot \ln(\tilde{C}_{ij}) \right)^2 \quad (15)$$

where the elements $\tilde{C}_{ij}$ are defined in Eq. (5). The performance of $D_n$ is shown in FIG. 12B, where it is clearly seen how the gap between triangles and circles (100 of each where used), increases with the number of pixels, n.

Figure 13A:
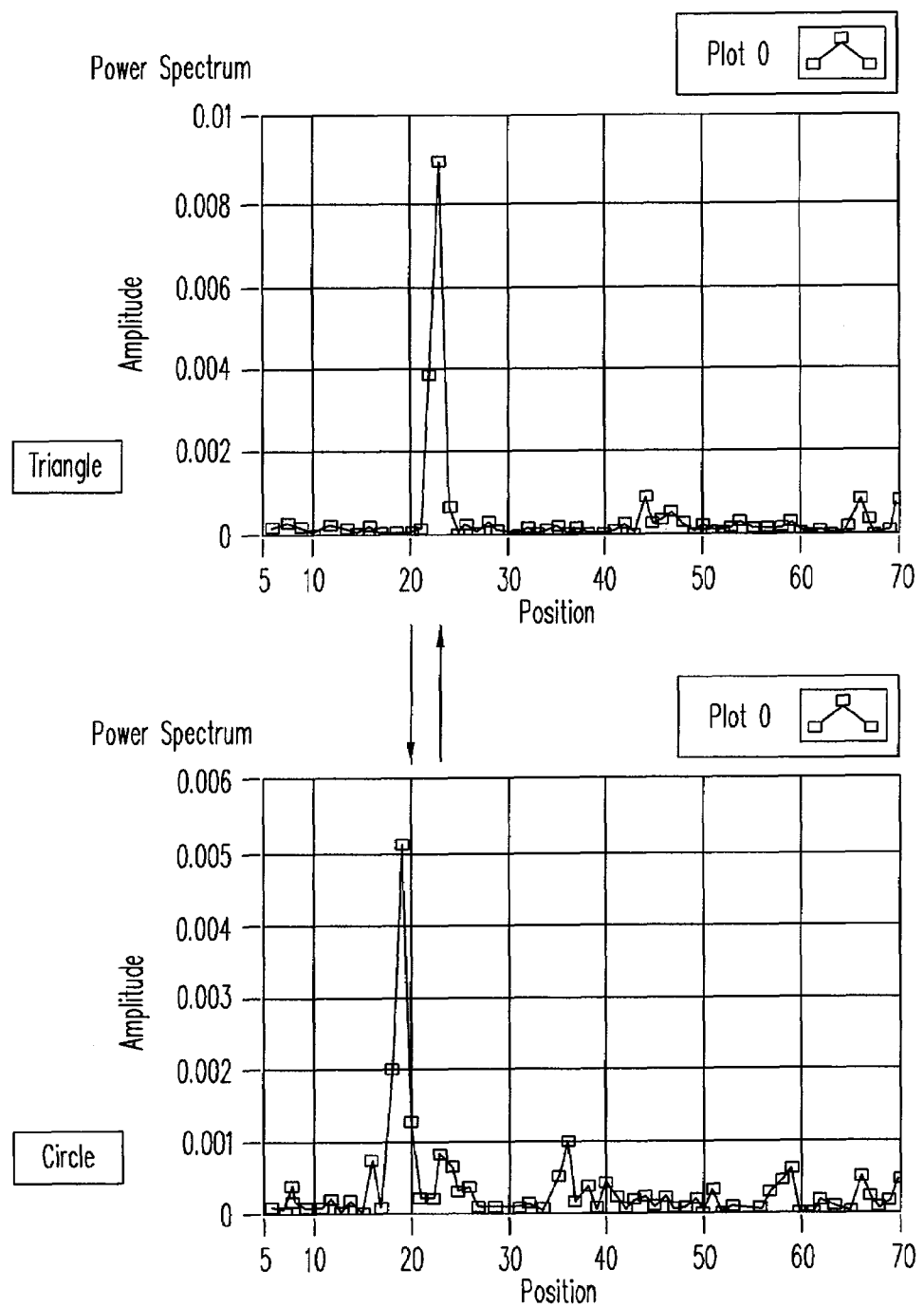
FIG. 13 shows linear operations which are carried out to discriminate between the circle and the triangle shown in FIG. 12A.
Figure 13B:
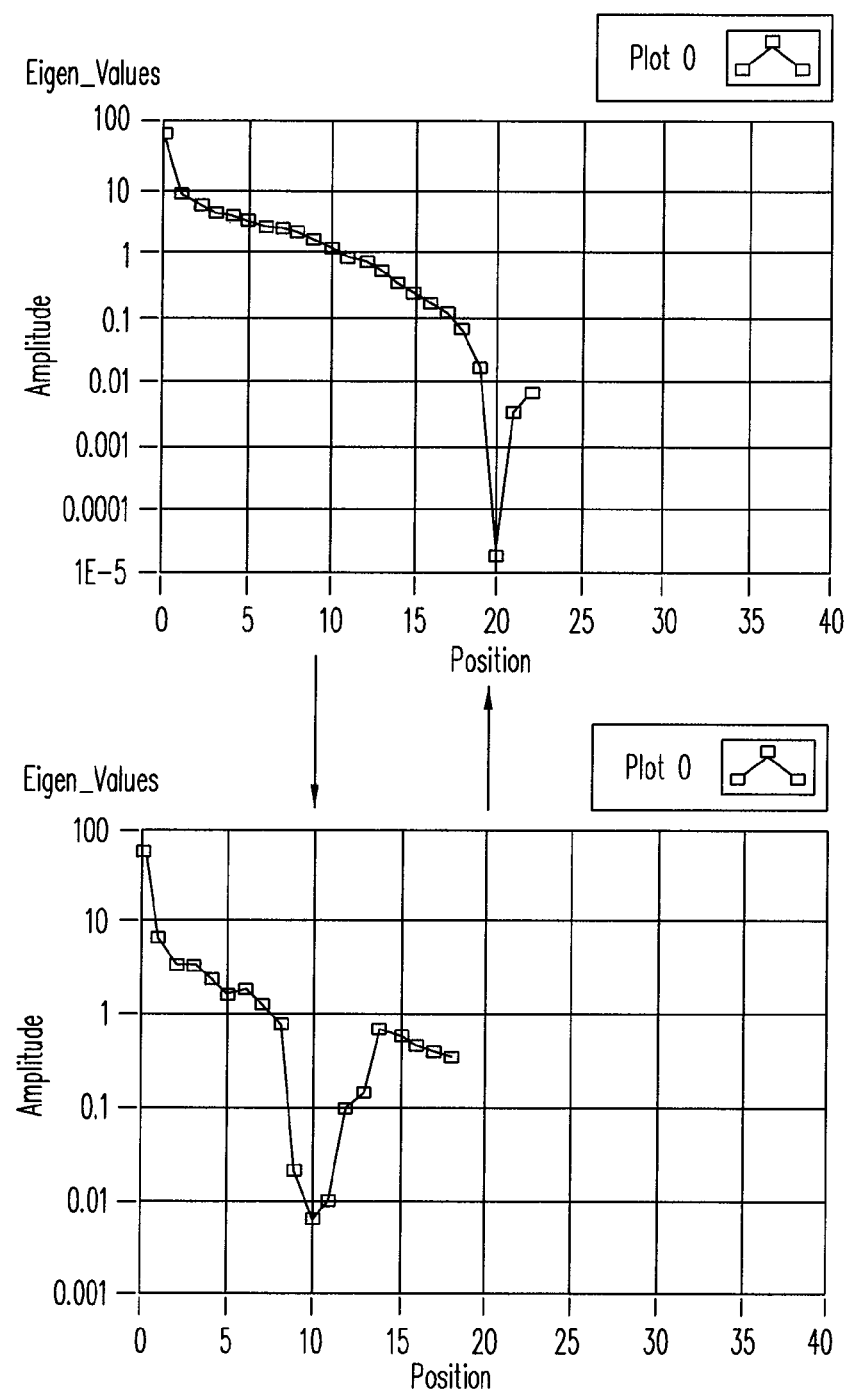
Figure 14A:
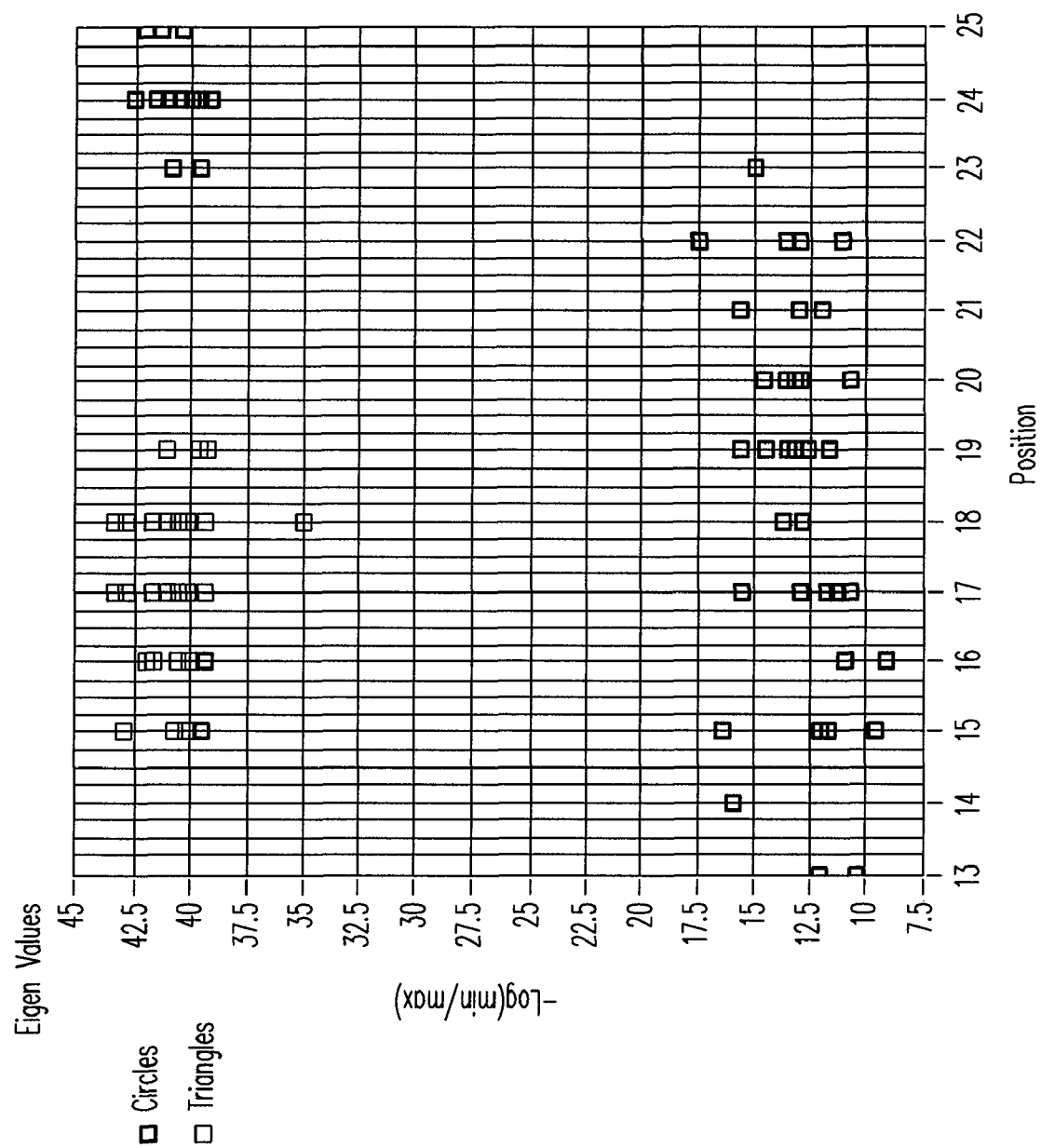
FIGS. 14A and 14B show plots of circles and triangles in the space domain and in the frequency domain to illustrate a method in accordance with this invention.
Figure 14B:
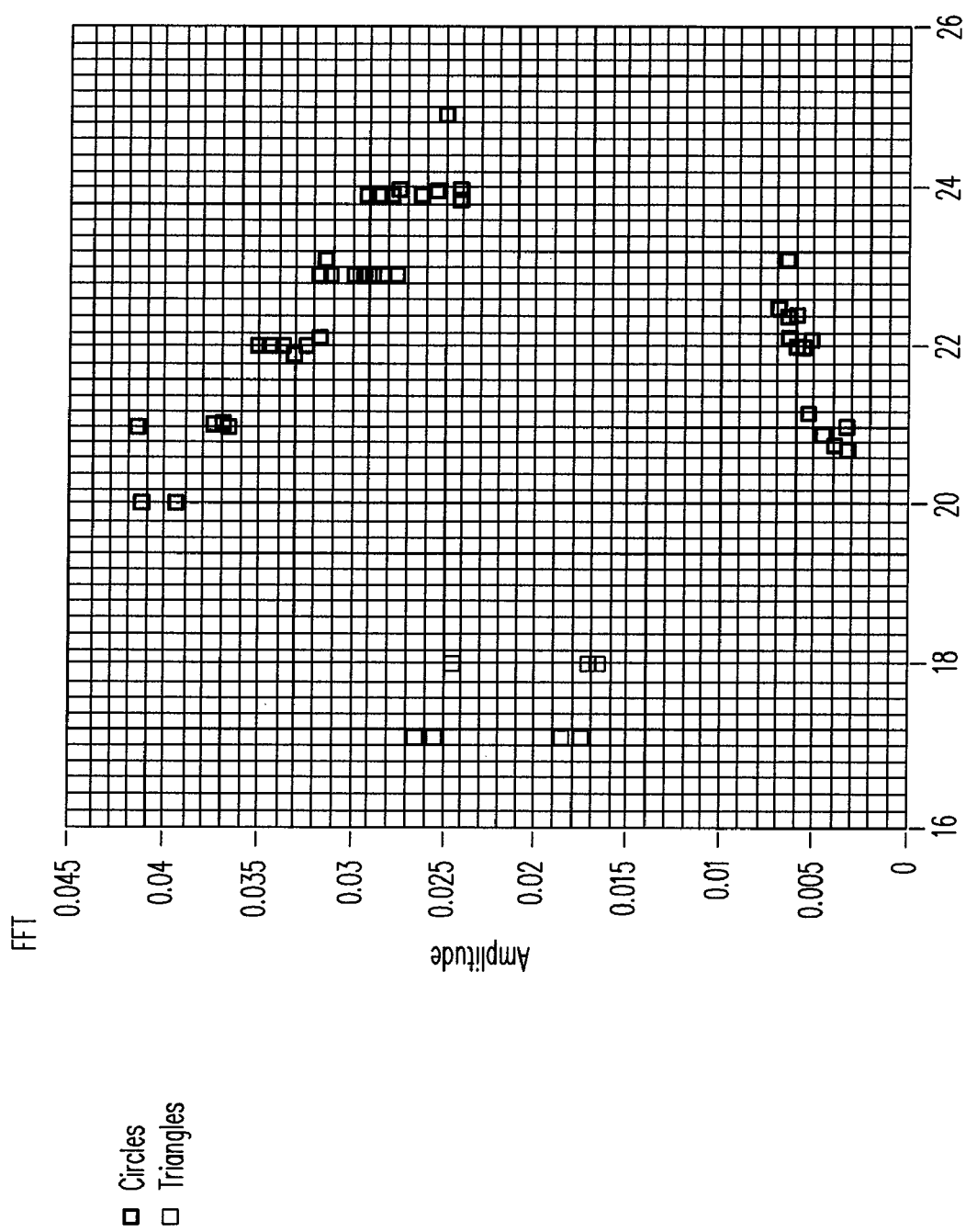

Equation (15) illustrates how a reduction in the dimensionality of the data, originally composed of 200 pixels, can be performed in order to accomplish a simple task such as the discrimination between the shape of a circle and/or a triangle. However, in order to make use of dPCA, a linear operation is needed. Two operations are suggested: Fourier Transform and Eigen-Value decomposition. This is illustrated in FIG. 13. In FIG. 13, it is shown that the triangular shape produces linear arrays with a 20% larger frequency tone, relative to a circle of the same area. By the same token, triangular figures give rise to an Eigen-value spectrum that has an "absorption" peak at a longer "wavelength", relative to circles of the same area. These two characteristics are illustrated in FIGS. 14A and 14B, where the eigen-value and frequencies plots are shown in a two-dimensional fashion, showing a clear discrimination between circles and triangles.

The present invention includes an algorithm that enables the well-known technique of Principal Component Analysis to be utilized in a fast and cost-effective manner. Typically, the data obtained by use of a structure such as disclosed in FIG. 5C (although other structures can be used also for this purpose) is analyzed and processed. By doing this, the Discrete Principal Component Analysis (dPCA) algorithm and structures used in connection with this algorithm, disclosed herein, allows the use and application of PCA techniques in sensing and imaging devices that can perform real time operations and multiple component identification. By uniquely combining principles of information entropy with principal component analysis, an optimum number of measurement channels n (between about six (6) to eleven (11)) has been found to be optimum for measuring the concentrations of glucose in water. This optimization technique applies equally to the measurement of other materials (i.e. principal components) in other mixtures. This invention makes possible the measurement of principal components in mixtures in an optimum manner using a minimum number of measurement channels without losing quality of performance, thus significantly lowering the cost and decreasing the time required to make the measurements compared to prior measurement techniques.

What is claimed is:

1. A method for using an optical system employing filtered broad band light to determine the specific components in a material sample, which comprises:

forming an n by r matrix C representing measurements made by the optical system of m samples of the material to be analyzed at n different light frequencies, each sample of the material containing r principal components, each sample containing known quantities of the r principal components in the material being analyzed where n is a finite number related to the number of measurement channels in the optical system and is selected to reduce the cost of the optical system and to increase the speed of measurement associated with the optical system while maintaining beneath a selected value the uncertainty associated with the measurements, measuring m different samples at n different frequencies using the optical system, each of said m samples containing unknown quantities of r specific components in the material, where "m" is a selected integer representing the number of samples and r represents the number of principal components in the material;

using the measured results from the m samples, each sample containing unknown quantities of the r principal components, to form an n by m matrix P, where P=C·R, where R is an r by m matrix representing unknown values of the r principal components which are being measured in the m material samples; and further wherein said matrix R is found from said matrix P and said matrix C as in the expression $R = (C^T \cdot C)^{-1} \cdot C^T \cdot P.$ 2. The method of claim 1 wherein said n different light frequencies are generated by passing broadband light through n different filters.

3. The method of claim 1 wherein said method provides one to two orders of magnitude reduction of parameter space dimensionality, n, in PCA problems.

4. The method of claim 1 wherein the computational operations of a given PCA problem are reduced by one to two orders of magnitude.

5. The method of claim 1 wherein the method provides an improvement of one to two orders of magnitude in precision over conventional PCA techniques using the same number of computational steps.

6. The method of claim 1 applied in connection with a selected one of a diverse number of measurement systems where PCA is the algorithm of choice, said system being selected from the group consisting of spectral analysis, image processing, and pattern recognition.

7. The method of claim 1 used in conjunction with Raman spectroscopy analysis for in-vivo and/or field applications.

8. The method of claim 1 used in conjunction with fluorescence spectroscopy analysis for in-vivo and/or field applications.

9. The method of claim 1 used in conjunction with near infrared-absorption (NIR) spectroscopy analysis for in-vivo and/or field applications.

10. The method of claim 1 used in Fourier Transform Infrared (FTIR) analysis for in-vivo and/or field applications.

11. The method of claim 1 used in rapid and cost effective pattern recognition analysis for in-vivo and/or field imaging applications.

12. The method of claim 1 including:

measuring the entropy variance associated with a given measurement configuration and using the measured entropy variance to select the range within which the optimum number of measurement channels can be determined; wherein said range for the optimum number of measurement channels is such that said entropy variance is substantially lower than other ranges of values of said number of measurement channels.

13. The method of claim 12 including selecting from within said range the optimum number of measurement channels to be used in measuring the components of said material sample.

14. An optical system employing filtered broad band light for determining the specific components in a material sample, which comprises:

means for forming an n by r matrix, C, representing measurements of a first set of m samples of the material to be analyzed at n different light frequencies, each sample in the first set of m samples containing known quantities of the principal components in the material being analyzed, where n is a finite number related to the number of measurement channels in the optical system and is selected to reduce the cost of the optical system and to increase the speed of measurement associated with the optical system while maintaining beneath a selected value the uncertainty associated with the measurements;

means for measuring a second set of m different samples at n different frequencies, each of said m samples in said second set containing unknown quantities of r principal components in the material, where m is a selected integer representing the number of samples and r represents the number of principal components in the material; and means for solving the equation P=C·R for R by inverting C in the equation P=C·R to yield $$R=(C^T \cdot C)^{-1} \cdot C^T \cdot P$$

thereby to determine the unknown quantities of the r principal components in the second set of m different samples.

15. The optical system as in claim 14 wherein the number of measurement channels is between about six (6) and about eleven (11).

16. The optical system as in claim 14 wherein the number of measurement channels is optimized to reduce the cost of the optical system and to decrease the time required for the optical system to measure the concentration of glucose in water.

17. The optical system as in claim 14 whereby r equals one (1).

18. The optical system as in claim 14 whereby r has a value given by $1 \leq r \leq 10$.

19. The optical system of claim 14 wherein said method provides one to two orders of magnitude reduction of parameter space dimensionality, n, in PCA problems.

20. The optical system of claim 14 wherein the computational operations of a given PCA problem are reduced by one to two orders of magnitude.

21. Optical system of claim 14 wherein the method provides an improvement of one to two orders of magnitude in precision over conventional PCA techniques using the same number of computational steps.

22. The optical system of claim 14 applied in connection with a selected one of a diverse number of measurement systems where PCA is the algorithm of choice, said system being selected from the group consisting of spectral analysis, image processing, and pattern recognition.

23. The optical system of claim 14 used in conjunction with Raman spectroscopy analysis for in-vivo and/or field applications.

24. The optical system of claim 14 used in conjunction with fluorescence spectroscopy analysis for in-vivo and/or field applications.

25. The optical system of claim 14 used in conjunction with near infrared-absorption (NIR) spectroscopy analysis for in-vivo and/or field applications.

26. The optical system of claim 14 used in Fourier Transform Infrared (FTIR) analysis for in-vivo and/or field applications.

27. The optical system of claim 14 used in rapid and cost effective pattern recognition analysis for in-vivo and/or field imaging applications.

28. The optical system of claim 14 including:

measuring the entropy variance associated with a given measurement configuration and using the measured entropy variance to select the range within which the optimum number of measurement channels can be determined; wherein said range for the optimum number of measurement channels is such that said entropy variance is substantially lower than other ranges of values of said number of measurement channels.

29. The optical system of claim 14 including selecting from within said range the optimum number of measurement channels to be used in measuring the components of said material sample.

30. The optical system of claim 14 wherein each of said n different light frequencies are selected by using a procedure comprising:

scanning the parameter space, $Q^L$, that defines the characteristics of an arbitrary set of n different light frequencies in the optical system, where L=f×n, and f is the number of characteristics associated with a single light frequency;

selecting the values of the L characteristics of said optical system such that the determinant of matrix, $\xi$, which contains $(C^T \cdot C)^{-1}$, is substantially greater than the corresponding determinant for any other set of L characteristics; thereby to maximize the precision of the optical measurements using the said number of optical filters with a specific set of characteristics; further wherein said scanning of the parameter space, $Q^L$, comprises a two-step scan;

the first step comprising selecting a first set of points in the parameter space, $Q^L$, around a central point, following a normal distribution of solid angular width $\Omega$ around a preferred direction $\theta$; wherein said preferred direction $\theta$ is a direction of substantially higher values of the determinant of said matrix, $\xi$, relative to other directions;

the second step comprising further selecting a second set of points in the parameter space, $Q^L$, randomly distributed around each of the points in the first set selected in said first step, and selecting one of said points in the second set for which the value of the determinant of said matrix, $\xi$, is substantially larger than for the other points in said second set;

finding a new preferred direction, from the direction formed between the center point of said first set of points, and the selected point from said second set of points;

finding a new center for the next step of the procedure in the vicinity of or exactly on the selected point of the second set of points;

repeating the above procedure until the optical system thus obtained has the desired uncertainty associated with the measurements.

31. A method for using an optical system employing filtered broad band light to determine a specific component in a material sample, which comprises:

forming an n by 1 matrix, C, representing measurements of m samples of the material to be analyzed at n different light frequencies, each sample of the material containing one principal component, each sample containing known quantities of said principal component in the material being analyzed, where n is a finite number related to the number of measurement channels in the optical system, measuring m different samples at n different frequencies, each of said m samples containing unknown quantities of a specific component in the material, where "m" is a selected integer representing the number of samples;

using the measured results from the m samples, each sample containing unknown quantities of said principal component, to form an n by m matrix, P, where P=C·R, where R is a 1 by m matrix representing unknown values of the principal component which are being measured in the m material samples;

solving the equation, P=C·R, for R, by inverting C in the equation P=C·R to yield $R=(C^T \cdot C)^{-1} \cdot C^T \cdot P$; and defining a parameter S to be given by equation (8) as follows $$S = \sqrt{\sum_i (1 - \kappa_i \cdot (A_i - B_i)/(A_i + B_i))^2} \qquad (8)$$

whereby in equation (8) $A_i$ is the signal passed through the $i^{th}$ filter $f_i$ from the sample and represents a given concentration of said principal component in said sample, and $B_i$ is the signal passed through the $i^{th}$ filter $f_i$ related to a reference sample;

obtaining the concentration [g] of said principal component from S, by using the linear expression $[g]=K_g \cdot S+b \qquad (9)$ where in equation (9), $K_g$ and b are correlation constants, and equation (9) expresses [g] as a nonlinear function of the signals measured from the sample, $\vec{A}^t=(A_1, A_2, \ldots, A_n)$ This clearly contradicts the basic assumption of PCA, as stated in Eq. (1);

assuming a low principal component concentration so that $\vec{A} \approx \vec{B}$ (i.e. $\vec{A}$ is approximately but not exactly equal to $\vec{B}$);

approximating equation (8) as equation 10, $$S \approx \sqrt{n} \cdot \left(1 + \frac{\vec{B}^T \cdot \vec{v}}{2} - \frac{\vec{A}^T \cdot \vec{v}}{2}\right) \qquad (10)$$

where in equation (10) the vector, $\vec{v}$, is given by $\vec{v}^t=(\kappa_1/B_1, \kappa_2/B_2, \ldots, \kappa_n/B_n); \qquad (11)$ making the following associations, $b=-k_g \cdot \sqrt{n}, \qquad (12.1)$ $(C^t \cdot C)^{-1} \cdot C^t = \frac{K_g}{2} [\vec{v}^t], \qquad (12.2)$ $P=[\vec{B}-\vec{A}], \qquad (12.3)$ $R=[g] \qquad (12.4)$ rewriting equation (9) for R=[g] as, $R=(C^T \cdot C)^{-1} \cdot C^T \cdot P \qquad (13)$ extracting matrix C, which in this case is a vector corresponding to the only principal component in the problem, from Eq. (12.2), as $$C = \left(\frac{2}{K_g}\right) \cdot (\vec{v} \cdot \vec{v}^t)^{-1} \cdot [\vec{v}] \qquad (14)$$

whereby the dPCA procedure has found the values of ($f_i$, $\delta f_i$, $\kappa_i$) such that the linearity in Eq. (9) is satisfied, and such that the error (variance) in the measurement, $\sigma_{max}$, is minimized, specifically, the use of definitions as in Eqs. (12.1, 12.2, 12.3, 12.4) and Eq. 13 to establish the validity of the dPCA assumption for low glucose principal component concentrations such that $\vec{A} \approx \vec{B}$ (i.e. $\vec{A}$ is approximately but not exactly equal to $\vec{B}$).

32. The method of claim 31 wherein said material samples comprise glucose in blood and thus said principal component is glucose and said reference sample is blood.

33. The method of claim 32 wherein the number of measurement channels, n, is between about six (6) and about eleven (11).

34. The method of claim 31 wherein said method provides one to two orders of magnitude reduction of parameter space dimensionality, n, in PCA problems.

35. The method of claim 31 wherein the computational operations of a given PCA problem are reduced by one to two orders of magnitude.

36. The method of claim 31 wherein the method provides an improvement of one to two orders of magnitude in precision over conventional PCA techniques using the same number of computational steps.

37. The method of claim 31 applied in connection with a selected one of a diverse number of measurement systems where PCA is the algorithm of choice, said system being selected from the group consisting of spectral analysis, image processing, and pattern recognition.

38. The method of claim 31 used in conjunction with near infrared-absorption (NIR) spectroscopy analysis for in-vivo and/or field applications.

39. The method of claim 31 used in Fourier Transform Infrared (FTIR) analysis for in-vivo and/or field applications.

40. The method of claim 31 including:
measuring the entropy variance associated with a given measurement configuration and using the measured entropy variance to select the range within which the optimum number of measurement channels can be determined; wherein said range for the optimum number of measurement channels is such that said entropy variance is substantially lower than other ranges of values of said number of measurement channels.

41. The method of claim 40 including selecting from within said range the optimum number of measurement channels to be used in measuring the components of said material sample.

42. The method of claim 31 wherein each of said n filters, $f_i$, having a center wavelength, $\lambda_c$, a bandwidth, $\Delta\lambda$, and a transmissivity, $\kappa_i$, are selected by using a procedure comprising:
scanning the parameter space, $Q^L$, that defines the characteristics of an arbitrary set of n optical filters in the optical system, where L=f×n, and f is the number of characteristics associated with a single filter;

selecting the values of the L characteristics of said optical system such that the determinant of matrix, $\xi$, which contains $(C^T \cdot C)^{-1}$, is substantially greater than the corresponding determinant for any other set of L characteristics; thereby to maximize the precision of the optical measurements using the said number of optical filters with a specific set of characteristics; further wherein said scanning of the parameter space, $Q^L$, comprises a two-step scan;

the first step comprising selecting a first set of points in the parameter space, $Q^L$, around a central point, following a normal distribution of solid angular width $\Omega$ around a preferred direction $\theta$; wherein said preferred direction $\theta$ is a direction of substantially higher values of the determinant of said matrix, $\xi$, relative to other directions;

the second step comprising further selecting a second set of points in the parameter space, $Q^L$, randomly distributed around each of the points in the first set selected in said first step, and selecting one of said points in the second set for which the value of the determinant of said matrix, $\xi$, is substantially larger than for the other points in said second set;

finding a new preferred direction, from the direction formed between the center point of said first set of points, and the selected point from said second set of points;

finding a new center for the next step of the procedure in the vicinity of or exactly on the selected point of the second set of points;

repeating the above procedure until the optical system thus obtained has the desired uncertainty associated with the measurements.

* * * * *